(12) United States Patent
Nakano et al.

(10) Patent No.: US 7,528,942 B2
(45) Date of Patent: May 5, 2009

(54) METHOD AND APPARATUS FOR DETECTING DEFECTS

(75) Inventors: Hiroyuki Nakano, Chigasaki (JP); Toshihiko Nakata, Hiratsuka (JP); Sachio Uto, Yokohama (JP); Akira Hamamatsu, Yokohama (JP); Shunji Maeda, Yokohama (JP); Yuta Urano, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 205 days.

(21) Appl. No.: 11/472,426

(22) Filed: Jun. 22, 2006

(65) Prior Publication Data
US 2006/0290923 A1    Dec. 28, 2006

(30) Foreign Application Priority Data
Jun. 22, 2005    (JP)    ............................. 2005-181400
Feb. 27, 2006    (JP)    ............................. 2006-049488

(51) Int. Cl.
G01N 21/88    (2006.01)
(52) U.S. Cl. .............. 356/237.3; 356/237.1; 356/237.2; 356/237.4; 356/237.5
(58) Field of Classification Search ... 356/237.1–237.6, 356/239.8; 250/559.41, 559.45, 559.31
See application file for complete search history.

(56) References Cited

U.S. PATENT DOCUMENTS

| | | | | | |
|---|---|---|---|---|---|
| 5,245,403 | A | * | 9/1993 | Kato et al. | ................ 356/239.8 |
| 5,264,912 | A | * | 11/1993 | Vaught et al. | ............. 356/237.5 |
| 5,903,342 | A | * | 5/1999 | Yatsugake et al. | ......... 356/237.4 |
| 6,104,481 | A | * | 8/2000 | Sekine et al. | ............. 356/237.5 |
| 6,144,446 | A | * | 11/2000 | Nagasaki et al. | .......... 356/237.3 |
| 6,411,377 | B1 | | 6/2002 | Noguchi et al. | |
| 6,608,676 | B1 | | 8/2003 | Zhao et al. | |
| 6,731,384 | B2 | * | 5/2004 | Ohshima et al. | ......... 356/237.2 |

(Continued)

FOREIGN PATENT DOCUMENTS

JP    62-089336    4/1987

(Continued)

*Primary Examiner*—Sang Nguyen
(74) *Attorney, Agent, or Firm*—Antonelli, Terry, Stout & Kraus, LLP.

(57) ABSTRACT

A method and apparatus for detecting defects are provided for detecting harmful defects or foreign matter with high sensitivity on an object to be inspected with a transparent film, such as an oxide film, by reducing noise due to a circuit pattern. The apparatus for detecting defects includes a stage part on which a substrate specimen is put and which is arbitrarily movable in each of the X-Y-Z-θ directions, an illumination system for irradiating the circuit pattern with light from an inclined direction, and an image-forming optical system for forming an image of an irradiated detection area on a detector from the upward and oblique directions. With this arrangement, diffracted light and scattered light caused on the circuit pattern through the illumination by the illumination system is collected. Furthermore, a spatial filter is provided on a Fourier transform surface for blocking the diffracted light from a linear part of the circuit pattern. The scattered and reflected light received by the detector from the specimen is converted into an electrical signal. The converted electrical signal of one chip is compared with that of the other adjacent chip. If these signals are not identical to each other, the foreign matter is determined to exist on the specimen in detection.

8 Claims, 26 Drawing Sheets

U.S. PATENT DOCUMENTS

| | | |
|---|---|---|
| 6,762,831 B2 | 7/2004 | Shibata et al. |
| 7,061,601 B2 * | 6/2006 | Meeks .................... 356/237.2 |
| 7,068,363 B2 * | 6/2006 | Bevis et al. .............. 356/237.5 |
| 7,148,138 B2 * | 12/2006 | Mimotogi et al. ........... 438/637 |
| 7,333,192 B2 * | 2/2008 | Nakano et al. ........... 356/237.2 |
| 7,369,223 B2 * | 5/2008 | Hamamatsu et al. ..... 356/237.2 |
| 2005/0052644 A1 | 3/2005 | Lewis et al. |

FOREIGN PATENT DOCUMENTS

| | | |
|---|---|---|
| JP | 63-135848 | 6/1988 |
| JP | 01-117024 | 5/1989 |
| JP | 05-218163 | 8/1993 |
| JP | 06-258239 | 9/1994 |
| JP | 06-324003 | 11/1994 |
| JP | 08-271437 | 10/1996 |

* cited by examiner

FIG. 8
(a)
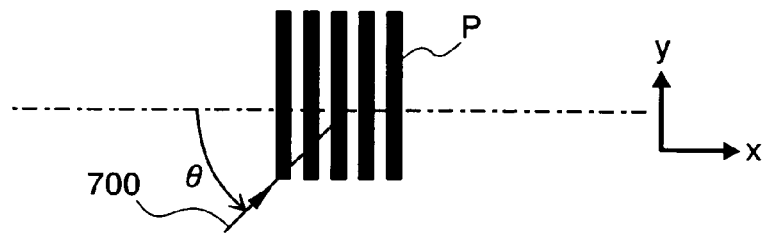
(b)
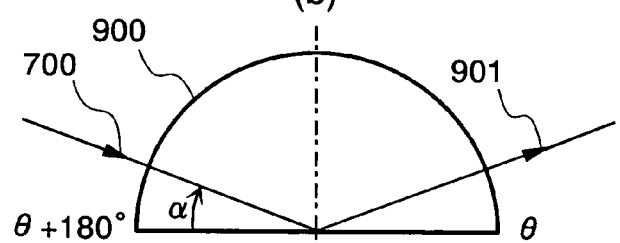
(c)
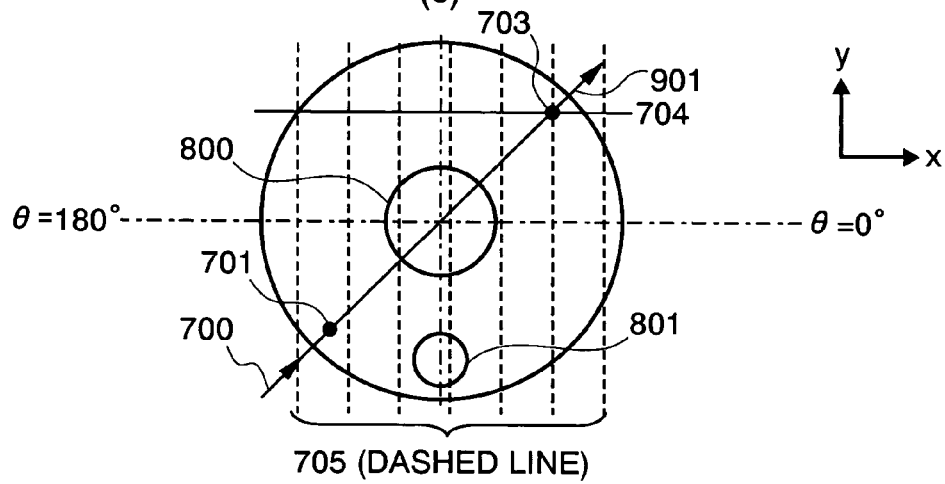
(d)
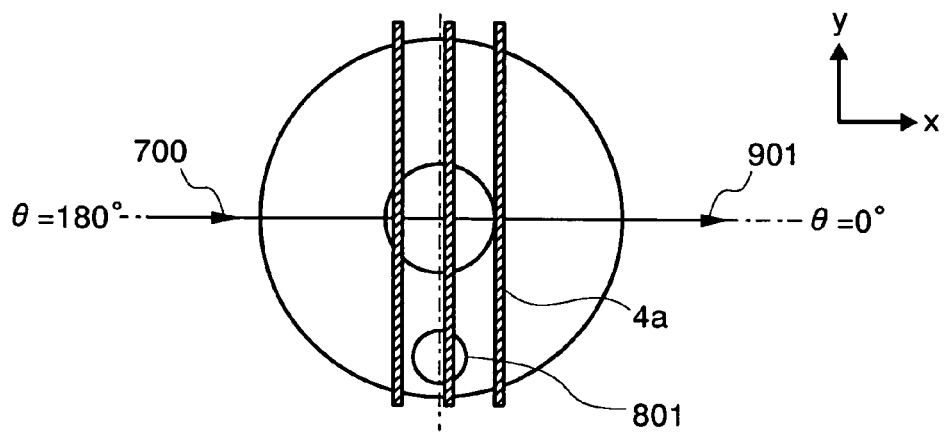

FIG.21
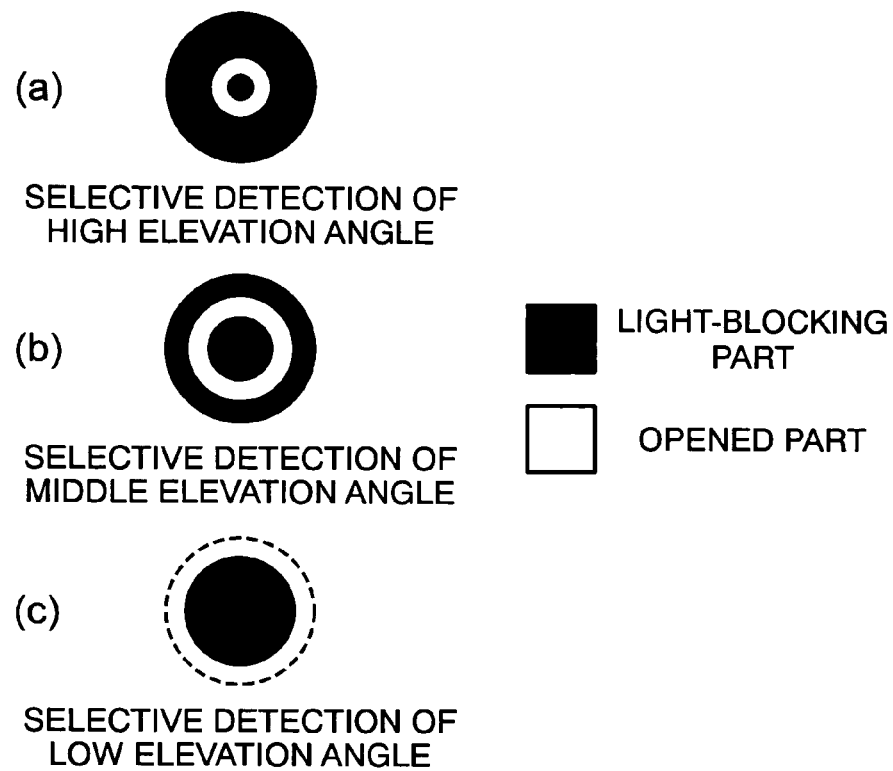
(a) SELECTIVE DETECTION OF HIGH ELEVATION ANGLE
(b) SELECTIVE DETECTION OF MIDDLE ELEVATION ANGLE
(c) SELECTIVE DETECTION OF LOW ELEVATION ANGLE
■ LIGHT-BLOCKING PART
□ OPENED PART
FIG.22
(a)
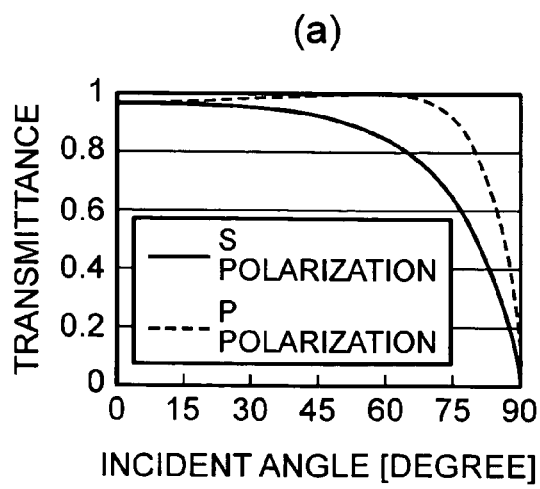
(a)
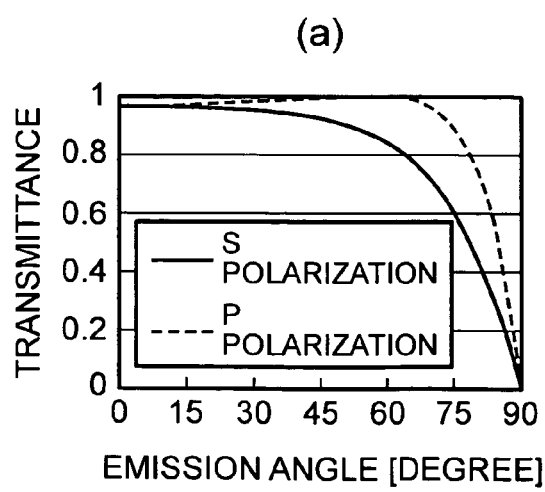

FIG.31
(a)
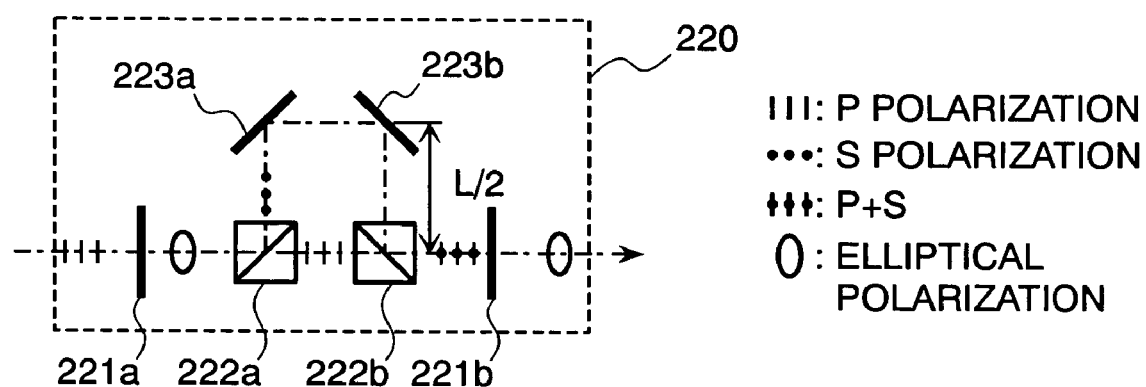
III: P POLARIZATION
•••: S POLARIZATION
╫: P+S
0 : ELLIPTICAL POLARIZATION
(b)
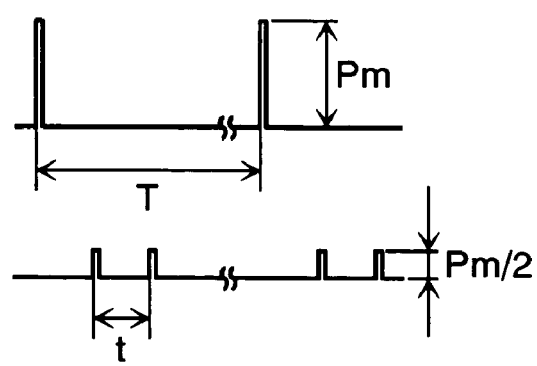

FIG.33
(a)
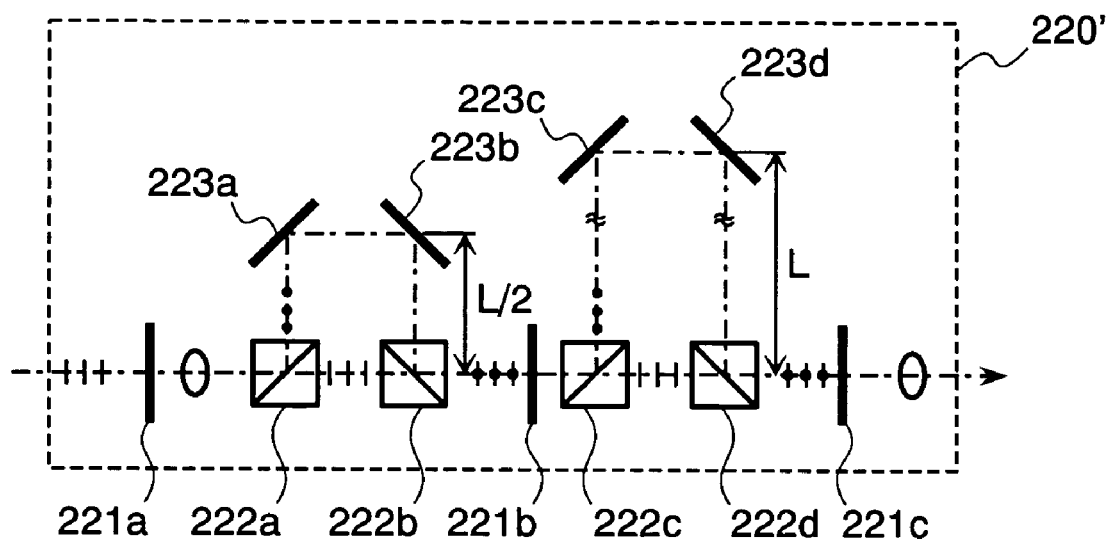
(b)
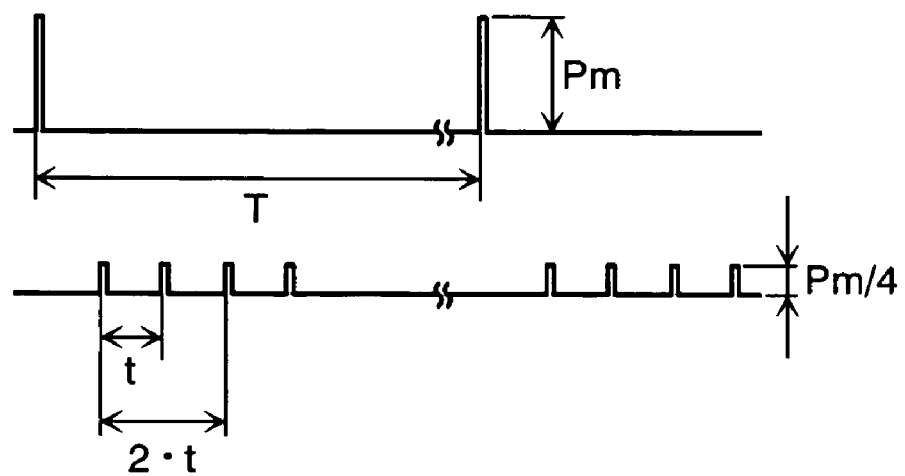

METHOD AND APPARATUS FOR DETECTING DEFECTS

BACKGROUND OF THE INVENTION

The invention relates to a method and apparatus for detecting defects which is adapted to detect a condition of occurrence of defects, such as foreign matter, in a manufacturing process of, for example, a semiconductor device, a liquid crystal display element, a printed board, or the like. The manufacturing process involves detecting a defect, e.g., foreign matter, caused in a step of forming a pattern on a substrate so as to manufacture an object of interest, and analyzing and remedying the defect.

In the conventional semiconductor manufacturing process, the presence of foreign matter on a semiconductor substrate (a substrate of interest to be inspected) may cause failures, including an electrical insulation failure, and short-circuit of wiring. Furthermore, when a semiconductor element is miniaturized to cause fine foreign matter in the semiconductor substrate, this foreign matter may cause the electrical insulation of a capacitor, or a breakage of a gate oxide film or the like. Such foreign matter may occur due to various causes, for example, from a movable part of a conveying device, from a human body, from a reaction with a process gas within a processing chamber, or from contaminant into a chemical agent or a material, and may be trapped into the semiconductor substrate in various forms.

Also, in the similar manufacturing process of the liquid crystal display element, the presence of any defects, such as contamination by foreign matter onto the pattern, may render the display element useless. The same holds true for the manufacturing process of the printed board, that is, the contamination by foreign matter may cause the short-circuit of the pattern, and the defective connection.

One of these kinds of conventional techniques for detecting foreign matter on a semiconductor substrate involves detecting scattered light generated from foreign matter by irradiating the semiconductor substrate with a laser beam when the foreign matter is attached thereto, and comparing a result of this detection with a result, of previous detection of the same kind of semiconductor substrate, as disclosed in, for example, JP-A No. 89336/1987. This technique can eliminate misinformation due to the pattern, and detect the foreign matter and defects with high sensitivity and high reliability. As disclosed in, for example, JP-A No. 135848/1988, another technique is known which involves detecting い゛scattered light generated from foreign matter by irradiating a semiconductor substrate with a laser beam when the matter is attached thereto, and analyzing the detected foreign matter using an analysis technique, such as a laser photo luminescence, or a two-dimensional X-ray analysis (XMR).

As another technique for detecting foreign matter, JP-A No. 218163/1993, and JP-A No. 258239/1994 disclose a method for detecting foreign matter and defects which involves irradiating a substrate of interest to be inspected, with coherent light linearly formed, removing the reflected and scattered light from a repetitive pattern on the substrate with a spatial filter, and emphasizing and detecting the non-repetitive foreign matter and defects.

Furthermore, a foreign matter detector is known in JP-A No. 117024/1989 which is adapted to irradiate a circuit pattern formed on the substrate of interest to be inspected, from the direction of an inclined angle of 45 degrees with respect to a main group of lines of the pattern such that the 0-order diffracted light from the main group of lines does not enter an aperture of an objective lens. The '163 patent discloses that diffracted light from a group of lines other than the main group of lines is also blocked by a spatial filter.

Other conventional techniques relating to a method and apparatus for detecting defects including foreign matter or the like are known in, for example, JP-A 324003/1994, JP-A 271437/1996, and U.S. Pat. No. 6,608,676.

In all the disclosures of the above-mentioned documents, however, a signal indicative of defects is missed due to scattered light from an irregular circuit pattern part, resulting in low sensitivity. On a transparent film, such as an oxide film, through which illuminating light passes, the brightness of the scattered light from the pattern is varied by a change in film thickness, which may further result in the lower sensitivity.

SUMMARY OF THE INVENTION

It is an object of the invention to provide a method and apparatus for detecting defects which can detect defects, such as fine foreign matter, at high speeds with high accuracy from a subject of interest for inspection with an oxide film through which illuminating light passes.

That is, in one aspect of the invention, a method for detecting a defect comprises the steps of irradiating a specimen with a circuit pattern including a repetitive pattern formed thereon, with light formed toward one direction in a long shape from an oblique direction, and detecting reflected and scattered light in a direction of a first elevation angle with respect to the specimen by blocking scattered light from the repetitive pattern among reflected and scattered light beams from the specimen irradiated with the light formed toward one direction in the long shape, thereby obtaining a first detection signal. The method also comprises the steps of detecting reflected and scattered light in a second elevation angle which is lower than the first elevation angle with respect to the specimen by blocking the scattered light from the repetitive pattern among the reflected and scattered light beams from the specimen irradiated with the light formed toward one direction in the long shape, thereby obtaining a second detection signal, and processing the first detection signal and the second detection signal to detect a defect including foreign matter on the specimen.

In another aspect of the invention, a method for detecting a defect comprises the steps of irradiating a specimen with a circuit pattern including a repetitive pattern formed thereon with first light formed toward one direction in a long shape from an oblique direction at a first azimuth angle, and irradiating an area on the specimen irradiated with the first light, with second light formed toward one direction in a long shape from an oblique direction at a second azimuth angle. The method further comprises the steps of detecting reflected and scattered light from the specimen irradiated with the first and second lights formed toward the respective directions in the long shape by blocking scattered light from the repetitive pattern, and processing a detection signal obtained by the detection to detect a defect including foreign matter on the specimen.

In another aspect of the invention, a method for detecting a defect comprises the steps of irradiating a specimen with a circuit pattern including a repetitive pattern formed thereon, with pulse laser light emitted from a light source from an oblique direction, detecting reflected and scattered light from the specimen irradiated with the pulse laser light by blocking scattered light from the repetitive pattern by a spatial filter, thereby obtaining a detection signal, and processing the detection signal to detect a defect including foreign matter on the specimen. The specimen is irradiated with the pulse laser light by dividing one pulse of the pulse laser light emitted from the light source into a plurality of pulses to decrease a peak value of the pulse laser light emitted from the light source.

In another aspect of the invention, an apparatus for detecting a defect comprises a light source adapted to emit illuminating light, table means for putting a specimen with a circuit pattern including a repetitive pattern formed thereon, irradiating means for forming the illuminating light emitted from the light source toward one direction in a long shape, and for irradiating the specimen put on the table means with the light formed from an oblique direction, and first detection means for detecting reflected and scattered light in a direction of a first elevation angle with respect to the specimen by blocking scattered light from the repetitive pattern among reflected and scattered light beams from the specimen irradiated with the light formed toward one direction in the long shape by the irradiating means. The apparatus also includes second detection means for detecting reflected and scattered light in a direction of a second elevation angle which is lower than the direction of the first elevation angle with respect to the specimen by blocking scattered light from the repetitive pattern among the reflected and scattered light beams from the specimen irradiated with the light formed toward one direction in the long shape by the irradiating means, and signal processing means for processing a first detection signal obtained by the detection of the reflected and scattered light by the first detection means and a second detection signal obtained by the detection of the reflected and scattered light by the second detection means, thereby detecting a defect including foreign matter on the specimen.

In another aspect of the invention, an apparatus for detecting a defect comprises a light source adapted to emit illuminating light, table means for putting a specimen with a circuit pattern including a repetitive pattern formed thereon, irradiating means for forming the illuminating light emitted from the light source toward one direction in a long shape, and for irradiating the specimen put on the table means with the light formed from an oblique direction, detection means for detecting reflected and scattered light from the specimen irradiated with the light formed toward the one direction in the long shape by the irradiating means by blocking scattered light from the repetitive pattern, and signal processing means for processing a detection signal obtained through the detection by the detection mean, thereby detecting a defect including foreign matter on the specimen. The irradiating means includes an optical path branching unit for branching an optical path of the illuminating light emitted from the light source into a plurality of optical paths, and a plurality of irradiating units for forming the lights which are branched into by the optical branching unit to enter the respective optical paths, toward respective directions in a long shape, and for irradiating the specimen with the lights from different azimuth angle directions.

Furthermore, in another aspect of the invention, an apparatus for detecting a defect comprises a light source adapted to emit illuminating light, table means for putting a substrate of interest to be inspected with a circuit pattern including a repetitive pattern formed thereon, first irradiating means for forming the illuminating light emitted from the light source toward one direction in a long shape, and for irradiating the specimen put on the table means with the light formed from an oblique direction at a first azimuth angle, and second irradiating means for irradiating an area on the specimen irradiated with the first light, with second light formed toward one direction in a long shape from an oblique direction at a second azimuth angle. The apparatus for detecting a defect also includes detection means for detecting reflected and scattered light from the specimen irradiated with the first light and the second light formed toward the respective directions in the long shape by the first irradiating means and the second irradiating means by blocking scattered light from the repetitive pattern, and signal processing means for processing a signal obtained through the detection by the detection means to detect a defect including foreign matter on the specimen.

In another aspect of the invention, an apparatus for detecting a defect comprises a light source adapted to emit illuminating light, table means for putting a specimen with a circuit pattern including a repetitive pattern formed thereon, irradiating means for irradiating the specimen put on the table means with the illuminating light emitted from the light source from an oblique direction, detection means for detecting reflected and scattered light from the specimen irradiated with the illuminating light by the irradiating means by blocking scattered light from the repetitive pattern by a spatial filter, and signal processing means for processing a detection signal obtained through the detection by the detection means to detect a defect including foreign matter on the specimen. The light source emits pulse laser light, and the irradiating means includes a pulse division unit for dividing one pulse of the pulse laser light emitted from the light source into a plurality of pulses, and is adapted to irradiate the specimen with the laser light whose pulse is divided into the plurality of pulses by the pulse division unit.

According to the invention, the diffracted light from the pattern can be reduced, and when the transparent film, such as an oxide film, is formed, the diffracted light from an underlying pattern can also be reduced. That is, although the intensity of the thin-film interference is changed due to variations in thickness of films between chips with the diffracted light from the underlying pattern serving as a secondary light source, variations in the intensity of detection signals between the chips due to this intensity change can be reduced. Thus, even under the presence of the transparent film, such as the oxide film, defects or fine foreign matter on a substrate, such as a LSI substrate W of interest to be inspected, can be detected at high speeds with high accuracy. Additionally, the foreign matter or defect on the transparent film can be detected and discriminated from the foreign matter or defect in or under the transparent film.

These and other objects, features and advantages of the invention will be apparent from the following more particular description of preferred embodiments of the invention, as illustrated in the accompanying drawings.

BRIEF DESCRIPTION OF THE DRAWINGS

FIG. 8A is a plan view of a pattern and showing a relationship between the pattern P and an illumination direction 700;

FIG. 8B is a diagram showing an imaginary spherical surface 900 on the substrate of interest to be inspected;

FIG. 8C is a plan view of the substrate of interest to be inspected, and showing emission of diffracted light by illumination at an illumination azimuth angle of 45 degrees;

FIG. 8D is a plan view of the substrate of interest to be inspected, and showing a relationship between a spatial filter and the substrate of interest to be inspected;

FIG. 21A is a plan view of a spatial filter for selective detection of a high elevation angle;

FIG. 21B is a plan view of a spatial filter for selective detection of a middle elevation angle;

FIG. 21C is a plan view of a spatial filter for selective detection of a low elevation angle;

FIG. 22A is a graph showing dependency of a transmittance of incident light into an interface of the transparent film, and of a transmittance of emitted light from the interface on an incident angle;

FIG. 22B is a graph showing dependency of a transmittance of the incident light into the interface of the transparent film, and of a transmittance of the emitted light from the interface on the emission angle;

FIG. 31A is a schematic front view showing a configuration of a pulse beam division optical system 200 which divides a pulse beam into two parts;

FIG. 31B illustrates a graph (on the upper stage) of the pulse shape of a pulse laser beam emitted from a light source 100, and a graph (on the lower stage) of the pulse shape of the pulse laser beam divided into two parts, and emitted from the pulse beam division optical system 200;

FIG. 33A is a schematic front view of a configuration of an optical system dividing a pulse beam into four parts, which system is a modification of the pulse beam division optical system 200; and FIG. 33B illustrates a graph (on the upper stage) of the pulse shape of a pulse laser beam emitted from the light source 100, and a graph (on the lower stage) of the pulse shape of a pulse laser beam emitted from a polarizing plate 221c and divided into four parts.

DESCRIPTION OF THE PREFERRED EMBODIMENTS

Exemplary preferred embodiments of the invention will be described hereinafter with reference to FIGS. 1 to 27.

Figure 1:
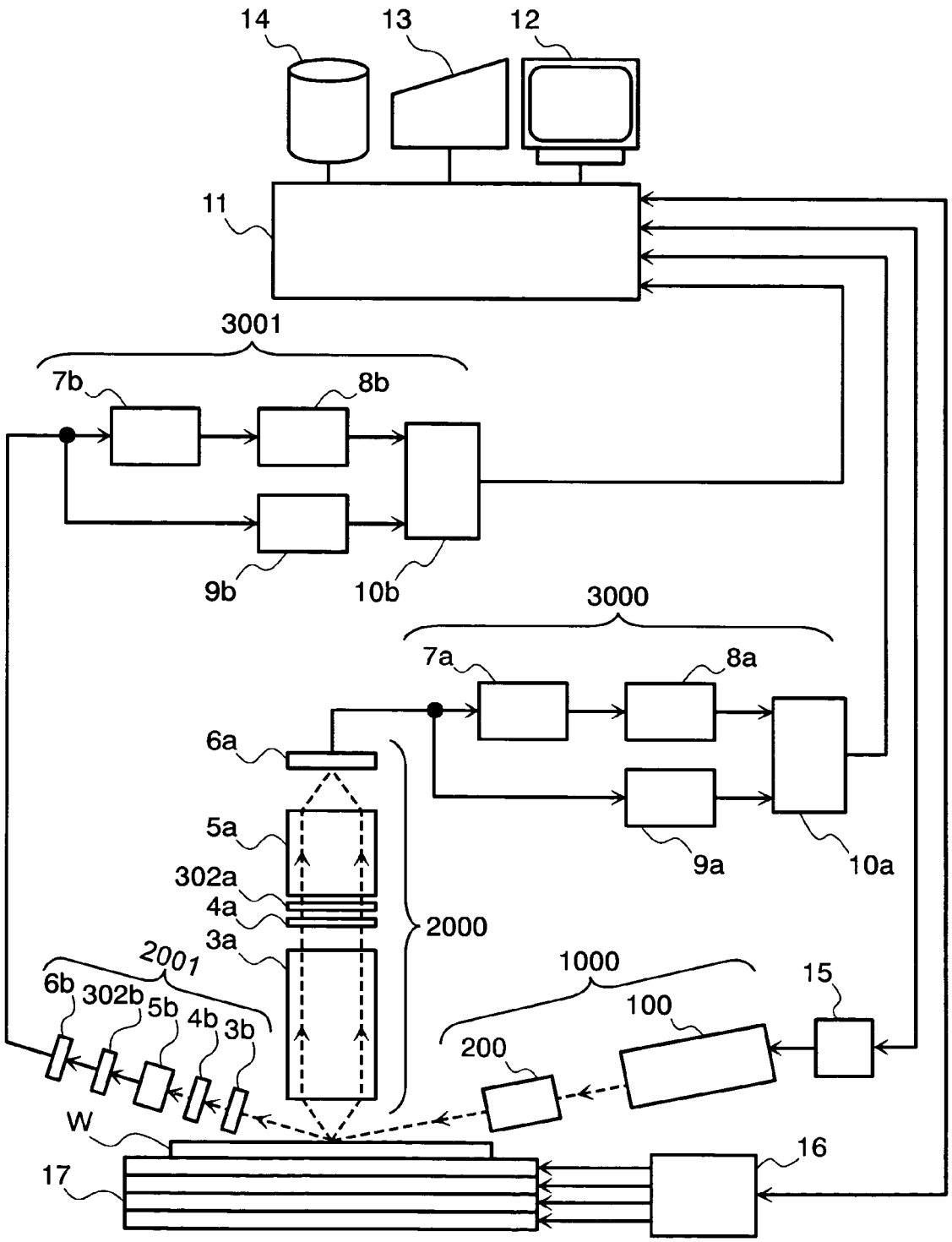
FIG. 1 is a schematic block diagram showing a structure of a defect detecting apparatus according to one embodiment.

FIG. 1 illustrates a schematic configuration of an apparatus for detecting defects, including foreign matter, according to one embodiment. The defect detecting apparatus includes an X-Y-Z-θ stage 17, an X-Y-Z-θ stage driver 16, an object to be inspected (a semiconductor substrate of interest to be inspected) W, a light source driver 15, an oblique illumination system 1000, an upward detection system 2000, an oblique detection system 2001, comparison processors for determination of defects 3000 and 3001, a computer 11, a display 12, a central processing unit 13, and a storage device 14.

The operation of the defect detecting apparatus will be described below. First, the substrate of interest to be inspected W mounted on the X-Y-Z-θ stage 17 is irradiated with light emitted from a light source 100 via an illumination optical system 200. Scattered light toward the upward detection system 2000 among scattered light beams from the subject W is collected by an objective lens 3a, and detected and photoelectrically converted by a detector 6a via a spatial filter 4a, a detection-light optical filter means 302a, and an image-forming lens 5a. On the other hand, scattered light toward the direction of the oblique detection system 2001 is collected by the objective lens 3b, and detected and photoelectrically converted by a detector 6b via the spatial filter 4b, an image-forming lens 5b, and a detection-light optical filter means 302b.

At this time, the scattered light from the foreign matter is detected, while horizontally moving the X-Y-Z-θ stage 17 with the substrate W mounted thereon, so that the result of detection can be obtained in the form of a two-dimensional image. The thus-obtained images pass through delay circuits 7a and 7b, and then are stored in respective memories 8a and 8b. Once the images detected from an adjacent chip are stored in memories 9a and 9b, the comparison circuits 10a and 10b respectively compare the images of the chip stored by the memories 8a and 8b with those of the same area of the adjacent chip stored by the memories 9a and 9b, thereby determining the presence of foreign matter or defects from the result of comparison. If diffracted and scattered light from the pattern is small enough, for example, because it is reduced by the spatial filters 4a and 4b, or by an illumination detection direction or selection of a polarization, the comparison process is not carried out, and a signal corresponding to a value equal to or above a threshold value can be determined to be associated with the defect. The result of determination is displayed on the display 12 or stored in the storage device 14 by the computer 11. Furthermore, information on the size and position of the foreign matter is specified by the central processing unit 13.

The illumination optical system 200 is configured to irradiate the substrate of interest to be inspected W with the light, using a beam expander, and a cylindrical lens, and adjusted such that focal points of the upward detection system 2000 and the oblique detection system 2001 are irradiated with the light. Note that in the embodiments, the light irradiated is a slit-like beam composed of substantially collimated light in the longitudinal direction.

Since a light source having a short wavelength is desired to be used as the illumination light source so as to improve the sensitivity of detection of foreign matter in selecting the light source 100, a YAG laser, an Ar laser, or a UV laser is appropriate. Furthermore, in order to manufacture the small-sized low-cost detecting apparatus, a semiconductor laser is also appropriate.

The upper detection system 2000 and the oblique detection system 2001 are configured to have the objective lenses 3a and 3b, and the image-forming lenses 5a and 5b such that the scattered light from the substrate W of interest for inspection among the light emitted from the oblique illumination system 1000 is collected and image-formed on the detectors 6a and 6b, respectively. The upward detection system 2000 and the oblique detection system 2001 constitute a Fourier transform optical system configured to optically process the scattered light from the substrate W, for example, to modify and adjust the optical properties by spatial filtering. When the spatial filtering is carried out as the optical process, the use of the collimated light beams as the illuminating light improves the detection characteristics of foreign matter. For this reason, the slit-like beam is used which is composed of the substantially collimated light in the longitudinal direction.

The detectors 6a and 6b are used to receive the scattered light collected by the upward and oblique detection systems 2000 and 2001, respectively, and to photoelectrically convert the light. The detectors 6a and 6b may include, for example, a TV camera, a CCD linear sensor, a TDI sensor, an anti-blooming TDI sensor, a photomultiplier array sensor, and the like.

In selection of the detectors 6a and 6b, when weak light is to be detected, the photomultiplier array sensor, or the CCD sensor having the electron multiplying function, such as an electron bombardment CCD (EBCCD), or an electron multiplying CCD (EMCCD), maybe used. In order to obtain the two-dimensional image at high speeds, the TV camera is desirable. When the upward detection system 2000 and the oblique detection system 2001 of the embodiment are of the image-forming type, the TV camera, the CCD linear sensor, the TDI sensor, the area CMOS sensor, or the linear CMOS sensor should be used. Particularly, in order to output signals at high speeds, a detector should be used which includes a plurality of signal output ports capable of outputting signals in parallel. When a dynamic range of light received by the detectors 6a and 6b is large, that is, when light whose intensity exceeds a saturation level of the sensor is incident, the use of the sensor with the anti-blooming function can prevent an influence of saturation pixels on surrounding pixels, thus enabling the detection of defects including foreign matter or the like in the vicinity of a saturation area. In particular, for the TDI sensor, the anti-blooming type is desirable.

The comparison processor for determination of defects 3000 compares the detection result of one chip with that of the corresponding area of the adjacent chip to determine the presence of defects or foreign matter. For example, a difference in detected image of the same area between the adjacent chips is calculated and binarized, and then the signal having a value that is equal to or more than the binarized threshold value is determined to indicate the presence of foreign matter. This comparison processor for determination of defects 3000 can measure the size of foreign matter from the size of the binarized signal. If diffracted and scattered light from the pattern is small enough as compared with the diffracted and scattered light from the defect, for example, because it is reduced by the spatial filters 4a and 4b, or by an illumination detection direction, or by selection of a polarization, the comparison process may not be carried out, and a signal having the value equal to or above the threshold value can be determined to be associated with the defect.

Now, the oblique illumination system 1000, the upward detection system 2000, and the oblique detection system 2001 will be described in detail with reference to FIGS. 2 to 18, and FIGS. 24 to 28.

FIG. 27A is a block diagram showing a configuration of the oblique illumination system 1000, and FIG. 27B is a block diagram showing a configuration of the upward detection system 2000 and the oblique detection system 2001. The oblique illumination system 1000 includes the light source 100, lens systems for forming the slit-like beam (200a, 200b, 201a, 201b), and an illuminating-light optical filter means 301 disposed on any one or more positions designated by the dotted line LSOF.

As the illuminating-light optical filter means 301, an optical element capable of adjusting the intensity of light, such as a ND filter, or an optical attenuator, or a polarization-optical element, such as a polarizing plate, a polarized beam splitter, or a wavelength plate, or a wavelength filter, such as a bandpass filter, or a dichroic mirror, can be used to control the light intensity, polarization characteristic, and wavelength characteristic of the illuminating light.

When a laser light source having high coherence is used as a light source, a speckle which may be noise in detection tends to occur. In order to reduce the speckle, a means for reducing coherency of the illuminating light may be provided as the illuminating-light optical filter means 301. For example, as measures for reducing the coherency, the following method may be used. The method may involves generating a plurality of luminous fluxes with different optical path lengths by use of a plurality of optical fibers having different optical path lengths from each other, a quartz plate, or a glass plate, and superimposing the luminous fluxes on one another. Alternatively, the method may involve using a rotating diffuser.

The upward detection system 2000 and the oblique detection system 2001 include Fourier transform lens systems (3a, 3b, 5a, 5b) for collecting and image-forming the detection light, spatial filters (4a, 4b) for blocking a specific Fourier component, and detection-light optical filter means (302a, 302b) disposed on any one or more positions designated by the dotted line LSOF. As the detection-light optical filter means 302a, 302b, an optical element capable of adjusting the intensity of light, such as the ND filter, or the optical attenuator, or a polarization-optical element, such as the polarizing plate, the polarized beam splitter, or the wavelength plate, or a wavelength filter, such as the bandpass filter, or the dichroic mirror, can be used to control the light intensity, polarization characteristic, and wavelength characteristic of the detection light.

When the upward detection system 2000 largely differs from the oblique detection system 2001 in the intensity of the detection light, one of the detection lights may deviate from the dynamic range of the sensor, and thus cannot be detected. In order to prevent this, respective attenuation factors of light intensity adjustment means used as the detection-light optical filter means (302a, 302b), such as the ND filter, or the optical attenuator, may be individually adjusted to keep the balance of the amounts of detection lights between the upward detection system 2000 and the oblique detection system 2001, using the same illuminating light for the upward and oblique detection systems 2000 and 2001, thereby performing simultaneous detection by the upward and oblique detection systems 2000 and 2001.

Figure 2:
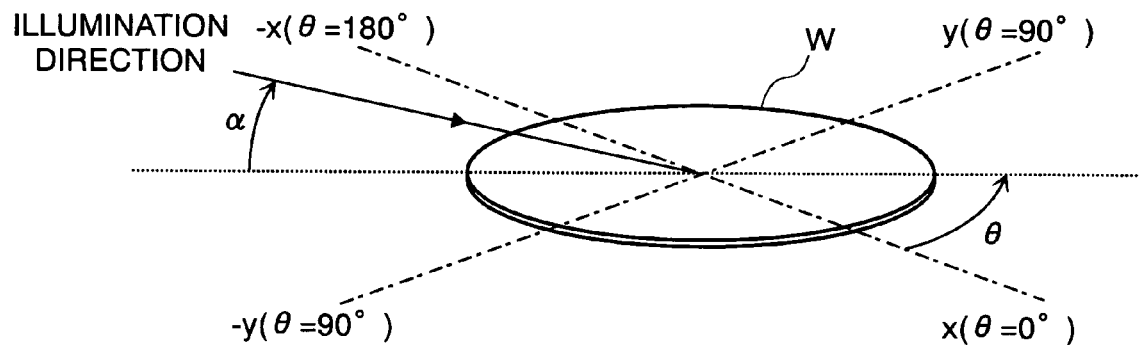
FIG. 2 is a perspective view of a substrate of interest to be inspected for explaining directions of illumination and detection.

FIG. 2 is a diagram for explaining an illumination direction and a detection direction with respect to the substrate of interest to be inspected W. In the figure, a direction of the main group of lines of the pattern formed on the substrate W, or a direction perpendicular to the direction of the main group of lines within the plane of the substrate W is referred to as an x direction, while a direction perpendicular to the x direction within the plane of the substrate W is referred to as a y direction. The slit-like beam composed of collimated light to the substantially longitudinal direction is formed by use of the oblique illumination system 100 so as to have a light beam traveling direction at an angle of θ (illumination azimuth angle) with respect to +x direction, and a longitudinal direction of the slit-like beam which is ±y direction within the x-y surface. The traveling direction of illumination has a predetermined tilt from a normal line of the substrate W of interest to be inspected. In the embodiment, the predetermined tilt is designated by an angle α from the substrate W (illumination elevation angle). The traveling direction of illuminating light is represented by the illumination azimuth angle θ and the illumination elevation angle α. Note that the reason why the illuminating light is formed in the form of the slit-like beam LS is that the high speed detection of defects, including foreign matter, is achieved. Also, the detection direction is represented by the detection azimuth angle and the elevation angle.

Figure 3:
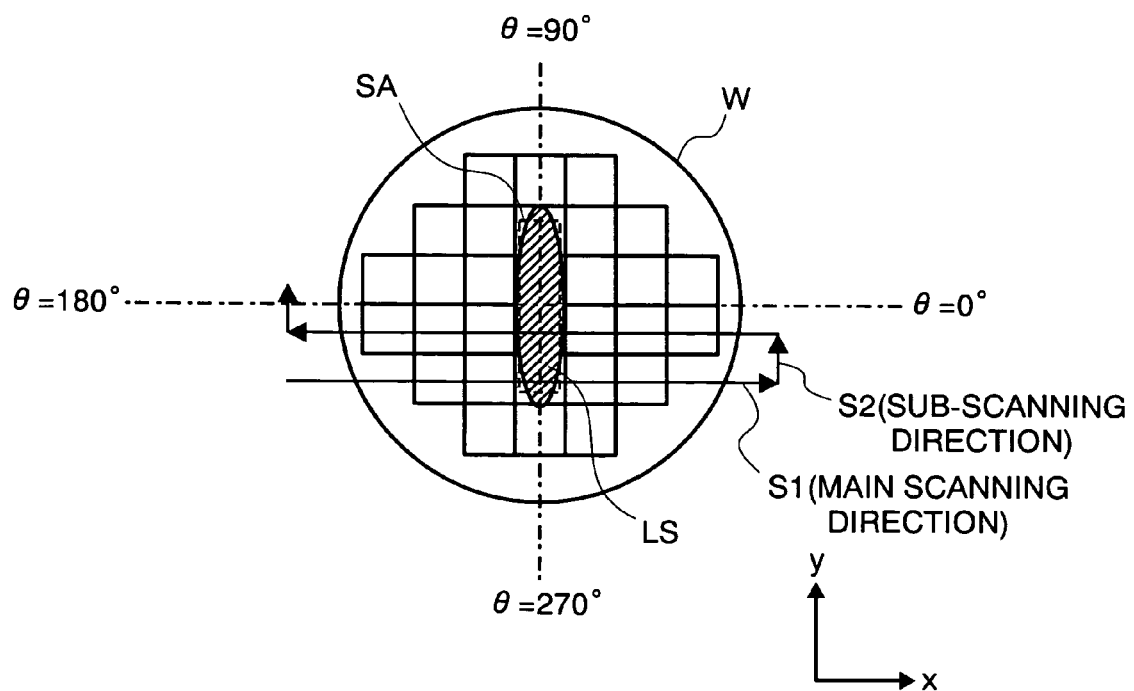
FIG. 3 is a plan view of the substrate of interest to be inspected, and showing a relationship among the shape of an illumination beam, a sensor detection area, and a scanning direction of a stage on the substrate of interest.

FIG. 3 illustrates a relationship among the slit-like beam LS composed of the collimated light substantially to the longitudinal direction, the sensor detection area SA, and the stage scanning direction S. The width of the sensor detection area SA in the longitudinal direction is included in the width of the illumination area LS of the slit-like beam composed of the substantially collimated light to the longitudinal direction. The scanning direction S in which the substrate W of interest to be inspected is put and traveled is defined by a main scanning direction (S1) as the x direction, and by a sub-scanning direction (S2) as the y direction. The illuminating light is applied such that the longitudinal direction of the slit-like beam LS composed of the substantially collimated light to the longitudinal direction is substantially vertical with respect to the main scanning direction S1 of the stage.

Figure 5:
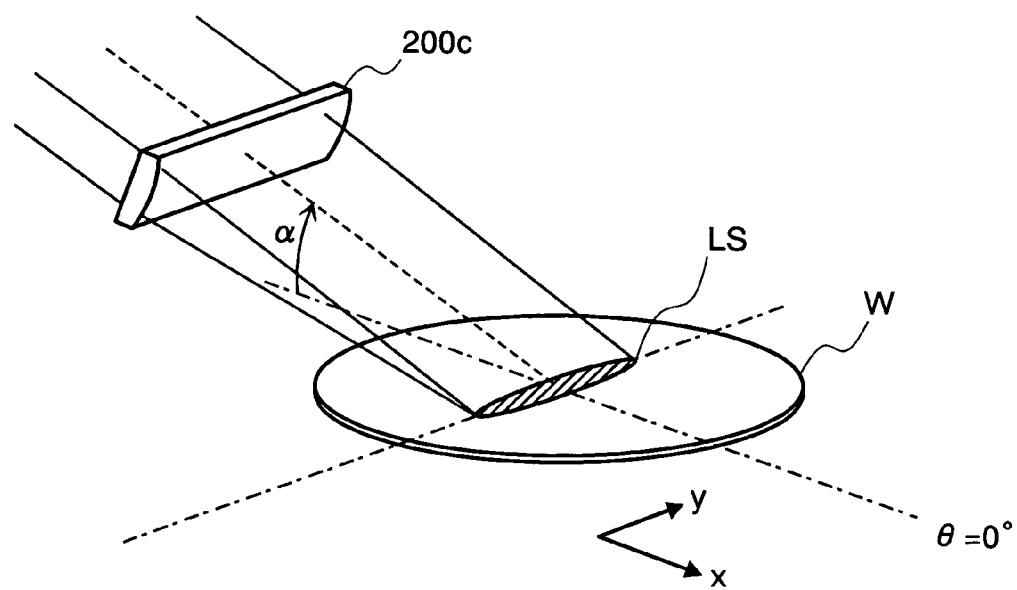
FIG. 5 is a perspective view of the substrate of interest to be inspected, and showing an illumination flux provided when the slit-like beam illuminates the substrate of interest using a cylindrical lens.

In the above-mentioned optical system, the substrate W of interest to be inspected is irradiated with the illuminating light at the angle α. FIG. 5 illustrates an illumination direction of the illuminating light when the illumination azimuth angle θ=0 degree.

Figure 6:
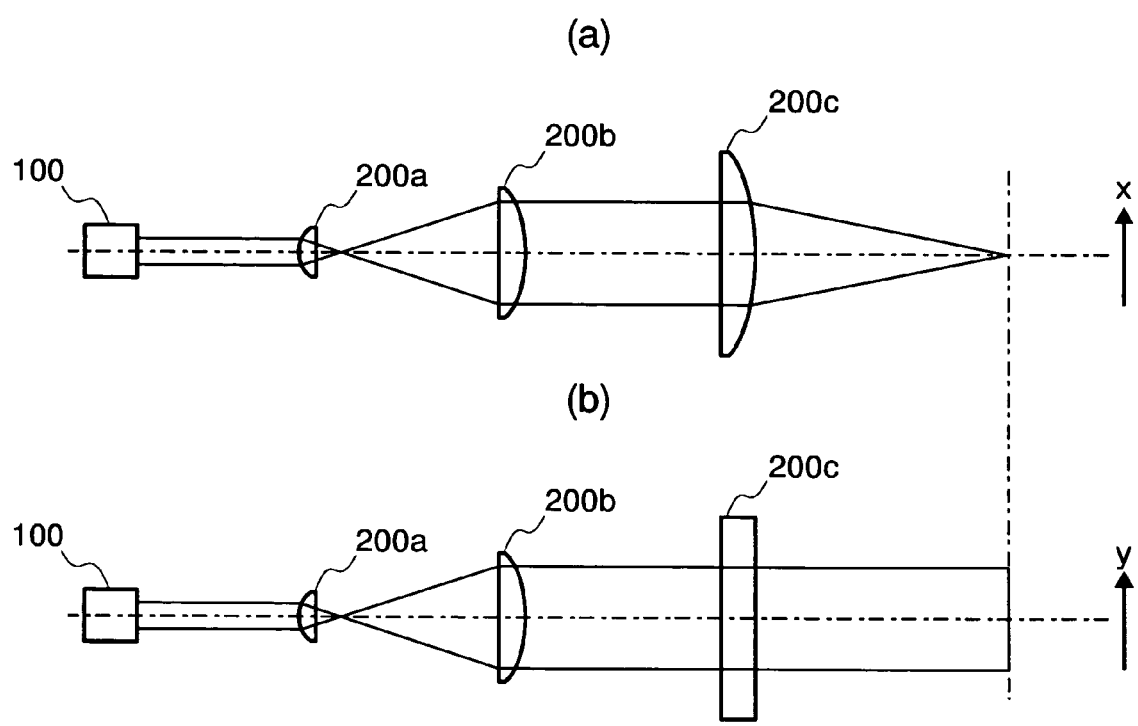
FIG. 6A is a schematic plan view showing a structure of an illumination optical system for illuminating the substrate of interest to be inspected with the slit-like beam.
FIG. 6B is a front view thereof.
Figure 14:
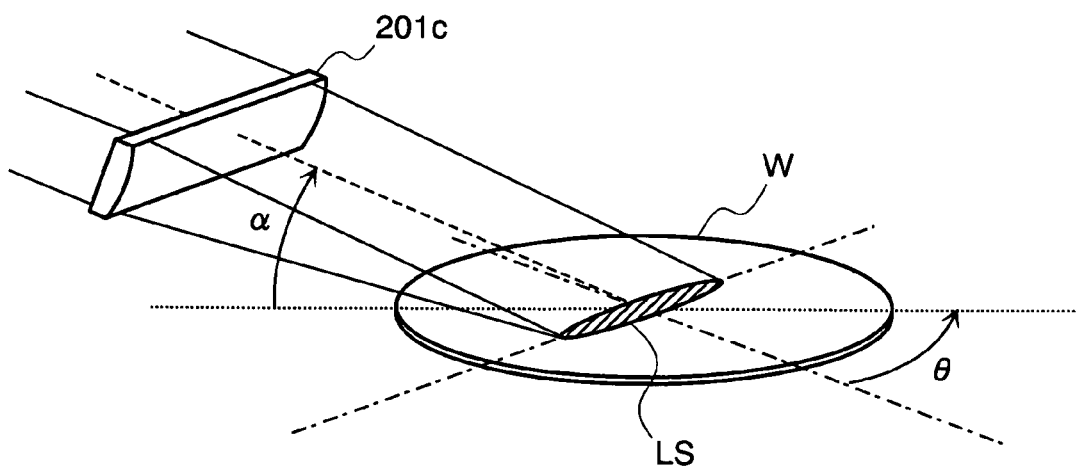
FIG. 14 is a perspective view showing an illumination luminous flux provided when a slit-like beam illuminates the substrate of interest for inspection in the direction of an angle of 45 degrees with respect to the horizontal direction using the cylindrical lens.
Figure 15:
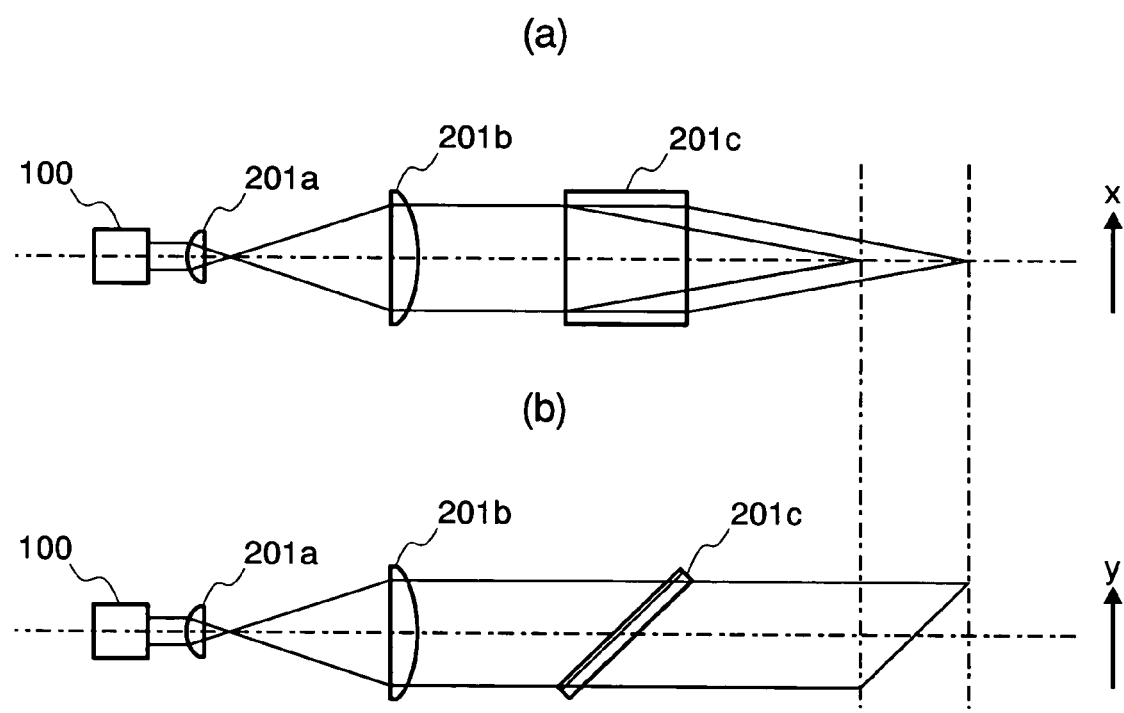
FIG. 15A is a schematic side view showing a structure of an illumination optical system adapted to cause a slit-like beam to illuminate the flat surface of the substrate of interest for inspection in the direction of an angle of 135 degrees with reference to the reference direction.
FIG. 15B is a schematic front view of the structure of the illumination optical system.

FIG. 6 illustrates an optical system adapted to emit the slit-like beam LS whose traveling direction is +x direction with its azimuth angle θ set to 0 degree, and which is composed of substantially collimated light in the ±y direction. Light emitted from the laser light source 100 is magnified by a beam expander composed of convex lenses 200a and 200b, and compressed in one direction by a cylindrical lens 200c. In the invention, the cylindrical lens 200c is used to achieve illumination which is critical in the x direction and collimated in the y direction. FIG. 14 is a perspective view for explaining illumination having an illumination azimuth angle θ, other than zero degree (θ=0), and FIG. 15 is a side view thereof (in the figure, θ=45 degrees). As shown in FIG. 15, by inclining the cylindrical lens, the illuminating light can enter the substrate W of interest for inspection at any azimuth angle θ, while maintaining the shape of the slit-like beam formed on the substrate of interest to be inspected W.

Figure 7:
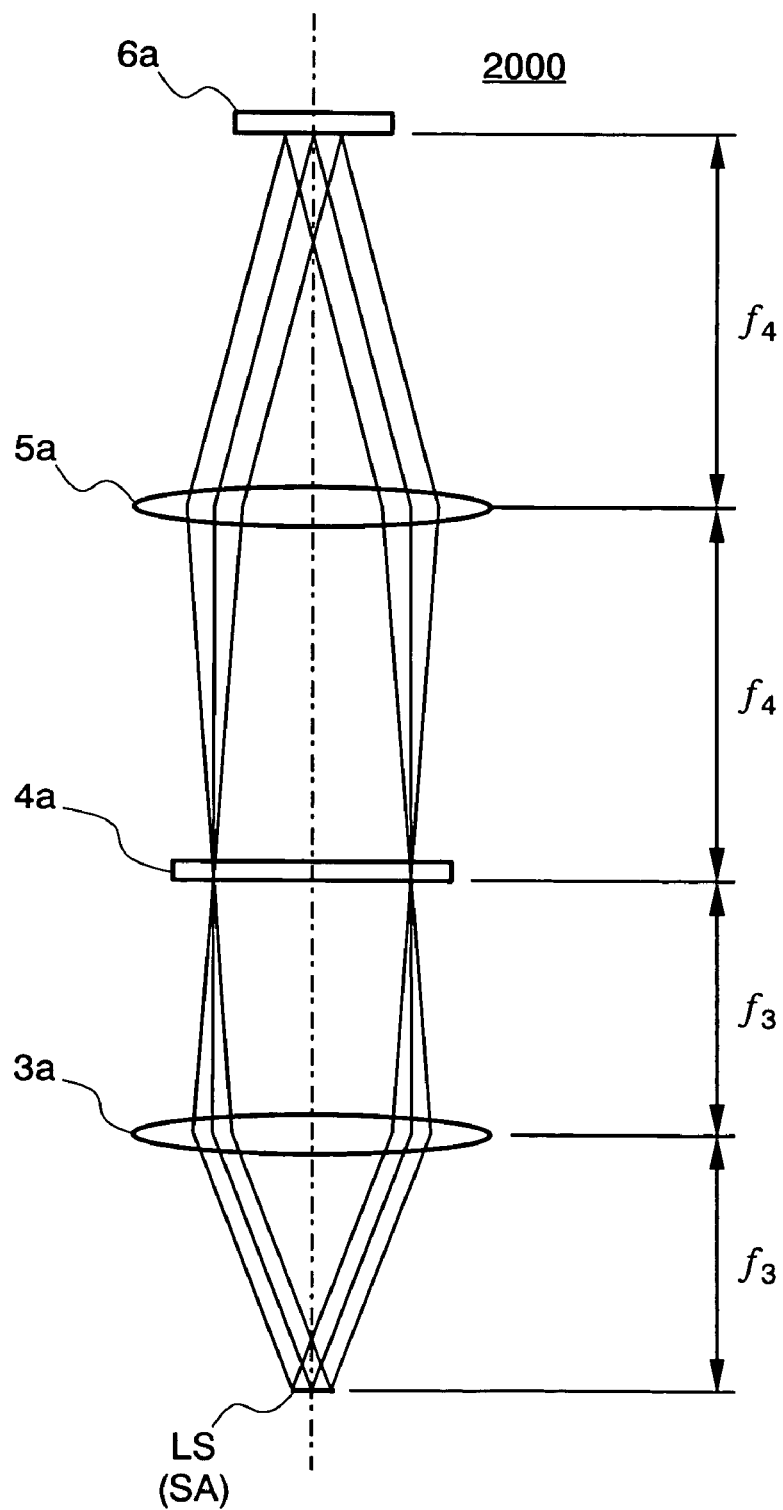
FIG. 7 is a schematic side view showing a structure of an upward detection optical system when an optical axis for detection is perpendicular to the substrate of interest to be inspected W.

FIG. 7 illustrates a configuration of the upward detection system 2000. The upward detection system 2000 is configured to collect the light emitted from the illumination area LS on the substrate W of interest for inspection by the objective lens 3a, and to detect the light by the one-dimensional detector 6a, such as the TDI sensor, through the spatial filter 4a for blocking a Fourier transform image of the reflected and diffracted light from the repetitive pattern, and the image-forming lens 5a. The spatial filter 4a is put at a spatial frequency area of the objective lens 3, that is, on an image-forming position for the Fourier transform (corresponding to an exit pupil) so as to block the Fourier transform image provided by the reflected and diffracted light from the repetitive pattern.

At this time, the beam LS of the illumination area on the substrate W of interest to be inspected as shown in FIG. 3 provides an image on the detector 6a by the objective lens 3a constituting a relay lens, and the image-forming lens 5a. That is, the area SA shown in FIG. 3 is a reception area of the one-dimensional detector 6a, such as the TDI sensor or the like.

The longitudinal direction of the slit-like beam LS is oriented in the arranging direction of chips with respect to the substrate W of interest to be inspected, and perpendicular to the main scanning direction S1. This is why the integral direction of the sensor 6a, which is the TDI sensor, can remain parallel to the traveling direction of the stage, the comparison of image signals between the chips can be performed in a simple way, while the calculation of coordinates of a defective position is also carried out easily, resulting in achieving the high speed detection of defects, including foreign matter.

Figure 4:
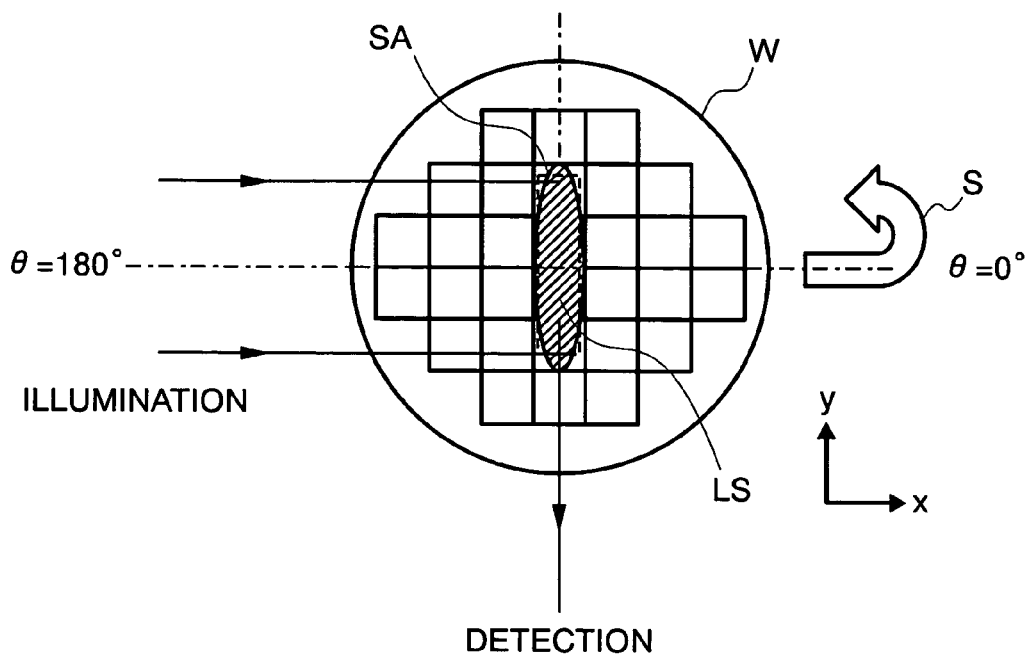
FIG. 4 is a plan view of the substrate of interest to be inspected, and showing a case where a slit-like beam illuminates the substrate of interest, and reflected and scattered light is detected from a longitudinal direction of the slit-like beam.

FIG. 4 is a plan view of a detection direction by the oblique detection system 2001 when the slit-like beam LS illuminates, and detection is carried out from the longitudinal direction of the slit-like beam LS (θ=90 degrees, or 270 degrees).

Figure 9:
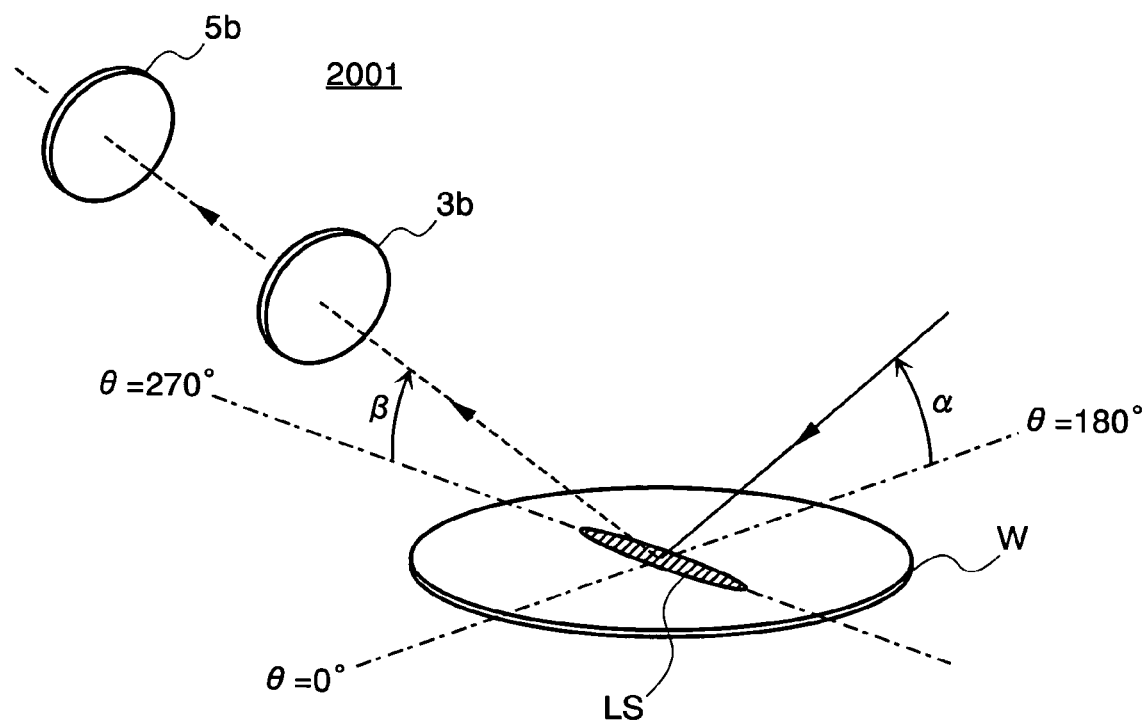
FIG. 9 is a schematic perspective view showing a structure of a detection optical system adapted for detection from the direction of an angle of 270 degrees with reference to a reference direction within a flat surface of the substrate of interest to be inspected.
Figure 10:
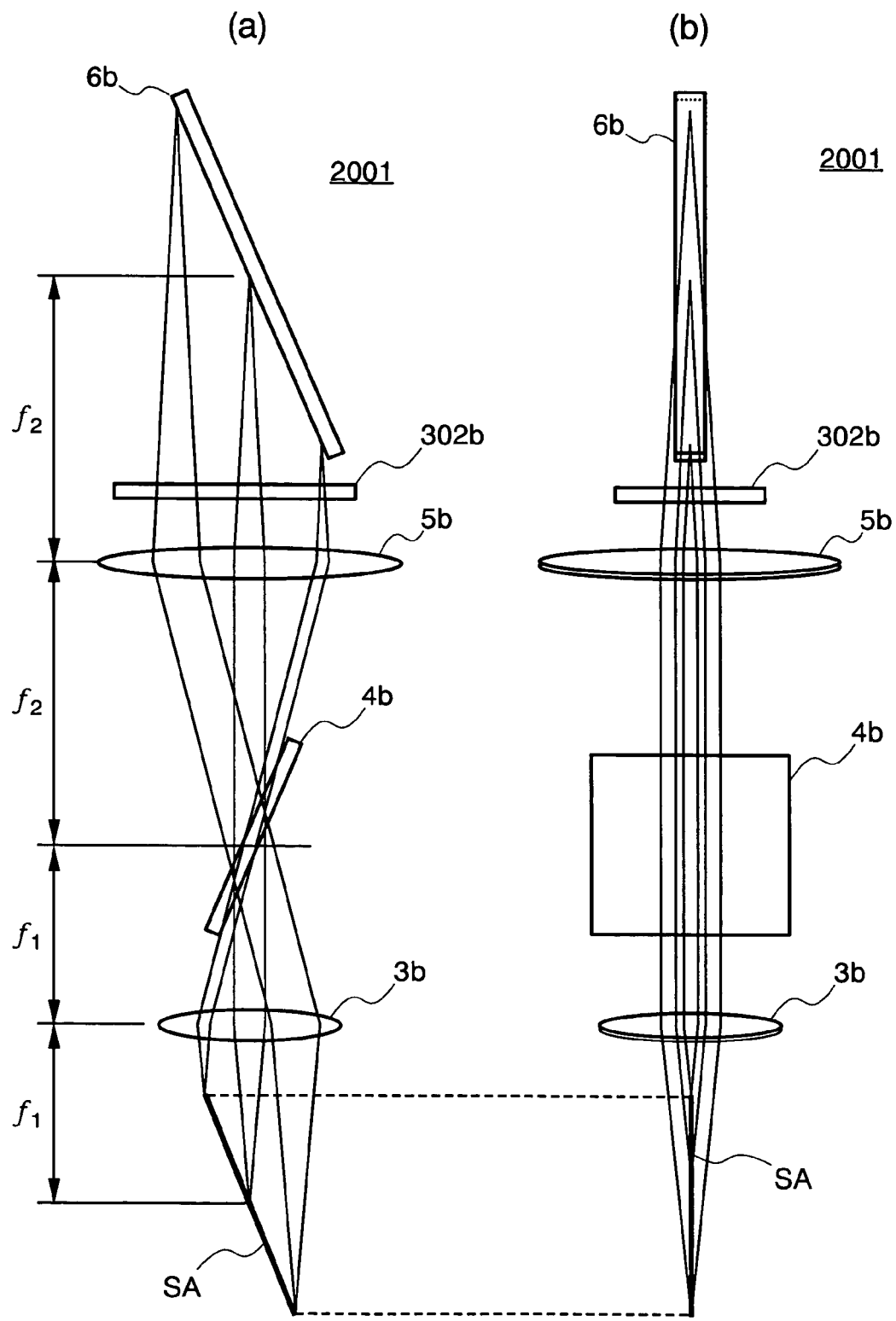
FIG. 10A is a schematic side view showing the structure of the detection optical system adapted for detection from the direction of an angle of 270 degrees with reference to the reference direction within the flat surface of the substrate of interest to be inspected.
FIG. 10B is a schematic front view of the structure of the detection optical system.

FIGS. 9 and 10 illustrate an example of the oblique detection system 2001 serving as an optical system of the embodiment. The oblique detection system 2001 is adapted to detect the substrate W of interest for inspection from the direction of an azimuth angle of 270 degrees, which substrate is irradiated with the slit-like beam LS. FIG. 10 illustrates a perspective view and a side view for explaining a schematic structure of the oblique detection system 2001. The oblique detection system 2001 is configured to collect the light emitted from the illumination area LS on the substrate W of interest for inspection by the objective lens 3b, and to detect the light by the one-dimensional detector 6b, such as the TDI sensor, through the spatial filter 4b for blocking a Fourier transform image of the reflected and diffracted light from the repetitive pattern, and the image-forming lens 5b. As shown in FIG. 10, by inclining the detector 6b in the longitudinal direction according to an inclination of the detection direction with respect to the substrate W of interest to be inspected, the light, which corresponds to the image on the substrate of interest for inspection W, can provide an image on the detector from the oblique direction.

FIGS. 24A and 24B illustrate a modified example of the oblique detection system 2000 which has been explained using FIGS. 9 and 10, for explaining the oblique detection system 2001 (1) serving as an optical system of the embodiment, for detecting the slit-like beam lS from the direction of an azimuth angle perpendicular to the longitudinal direction thereof (θ=0 degree, or 180 degrees). The oblique detection system 2001(1) is configured to collect the light emitted from the illumination area LS on the substrate W of interest for inspection by the objective lens 3b(1), and to detect the light by the one-dimensional detector 6b(1), such as the TDI sensor, through the spatial filter 4b(1) for blocking a Fourier transform image of the reflected and diffracted light from the repetitive pattern, and the image-forming lens 5b(1). When the detector 6b (1) is the one-dimensional detector, the y' direction of FIG. 24A is the longitudinal direction of the detector 6b (1). As shown in FIG. 24B, by inclining the detector 6b (1) in a direction perpendicular to the longitudinal direction according to the inclination (β) of the detection direction with respect to the substrate W of interest to be inspected, an image provided on the substrate W of interest to be inspected can be formed on the detector 6b (1) from the oblique direction.

In the above-mentioned method, the smaller the elevation angle of detection β, the larger the incident angle of the detection light into a sensitive surface of the detector 6b(1). In this case, some rate of the detection light is reflected depending on the characteristics of the sensitive surface of the detector 6b (1), thereby resulting in insufficient sensitivity.

The use of the oblique detection system 2001 (2) shown in FIGS. 25A and 25B can install the detector 6b(2) in a direction perpendicular to the detection light, without inclining the detector 6b(1) as explained in FIGS. 24A and 24B, thereby preventing a decrease in sensitivity due to the inclined entry of the light into the sensitive surface. In the oblique detection system 2001 (2) having the structure shown in FIGS. 25A and 25B, the light emitted from the illumination area LS on the substrate W of interest to be inspected is collected by the objective lens 3b(2), and detected by the one-dimensional detector 6b(2), such as the TDI sensor, through the spatial filter 4b(2) for blocking a Fourier transform image of the reflected and diffracted light from the repetitive pattern, the image-forming lens 5a (2), and the detection-light optical filter means 302b (2). A substantial detection area SA2 of the oblique detection system 2001(2) corresponds to the detection area SA on the surface of the object on the substrate W of interest to be inspected, and a focus thereof deviates by an inclination due to the detection elevation angle β in a position apart from the center of a field of view. For this reason, in the oblique detection system 2001 (2) shown in FIGS. 25A and 25B, the two-dimensional detector, or the TDI sensor the number of whose accumulated stages needed for forming a two-dimensional image is large is not appropriate for the detector 6b (2). However, for the one-dimensional detector, such as the linear CCD, or the TDI sensor the number of whose accumulated stages is small, the field of view in the x direction is narrow, and a deviation in focus is small as compared with a focal depth determined by the NA of the objective lens 3b (2) and the wavelength, which has a small influence on blurring of the image. This enables detection by the image forming process.

Figure 25:
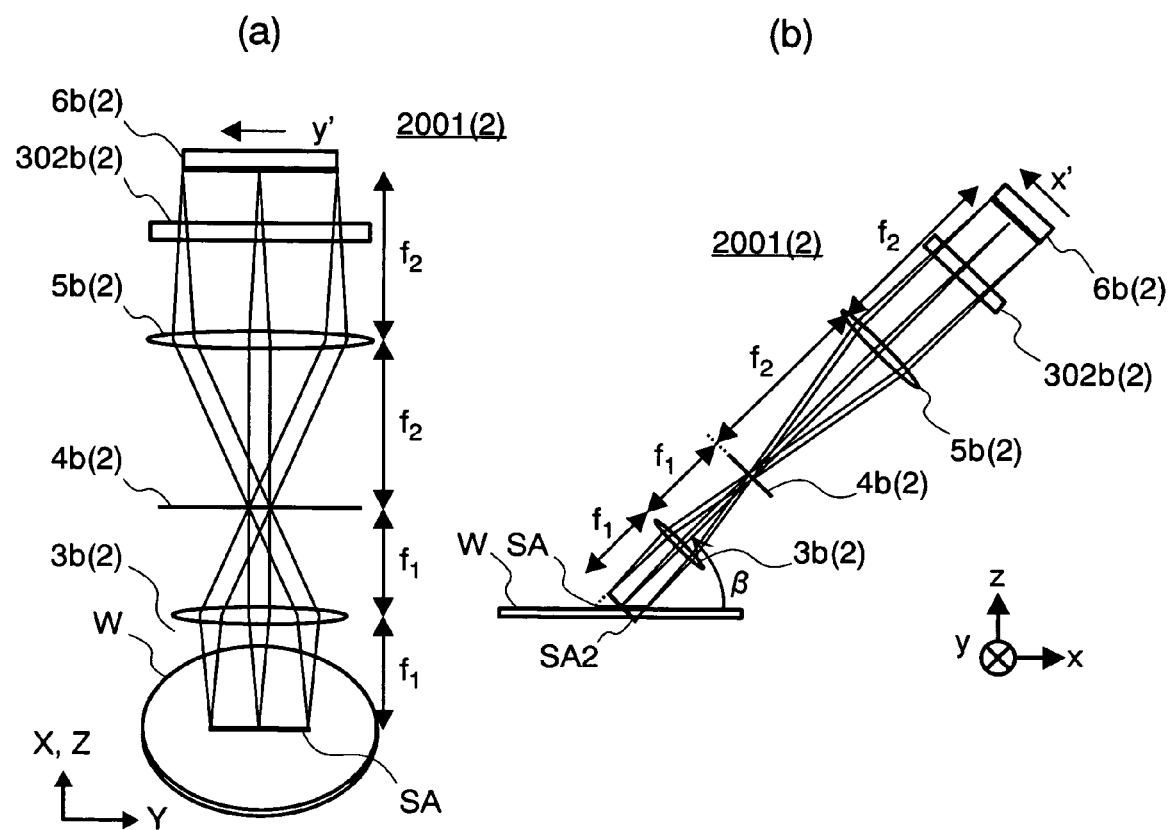
FIG. 25A is a perspective view of a detection optical system 2001(2) adapted for detection from the direction of an angle of zero degree with respect to the reference direction within the flat surface of the substrate of interest to be inspected.
FIG. 25B is a side view of the detection optical system 2001(2)
Figure 26:
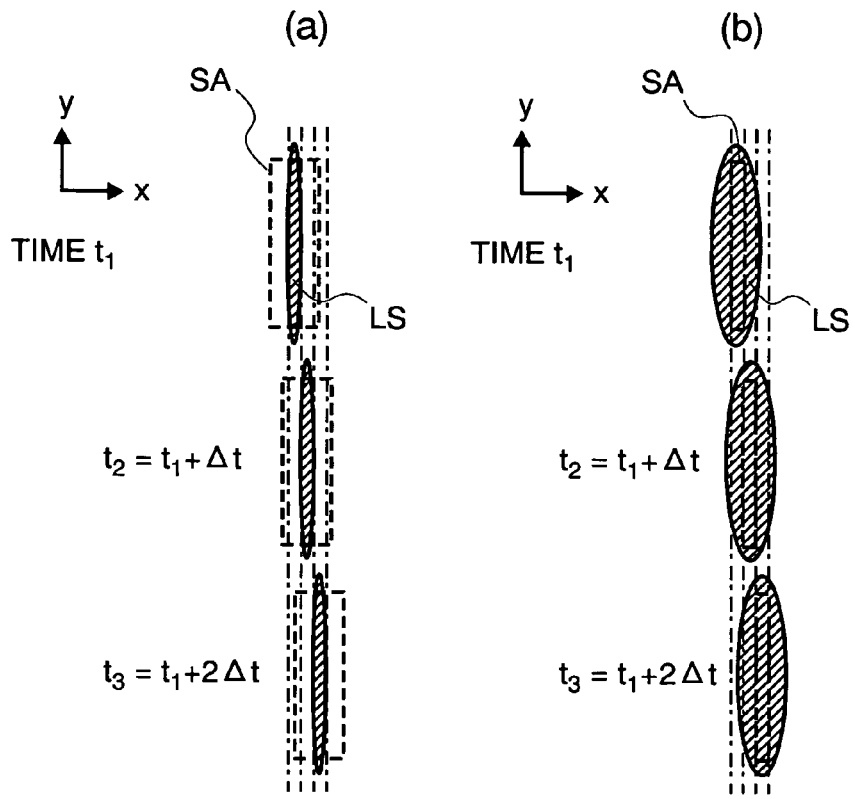
FIG. 26A is a diagram showing a relationship between the width of the shape of a slit-like beam in the x direction on the substrate of interest to be inspected, and the width of a detection area in the x direction, and showing that the width of the shape of the slit-like beam of illuminating light LS in the X direction is narrower than that of the detection area SA, and the width of a detection pixel is defined by the illuminating light by accumulating signals every distance corresponding to the illumination width.
FIG. 26B is a diagram showing a relationship between the width in the x direction of the shape of the slit-like beam on the substrate of interest to be inspected and the width of the detection area in the X direction, wherein the width of the shape of the slit-like beam of illuminating light LS in the x direction is wider than that of the detection area SA.
Figure 27:
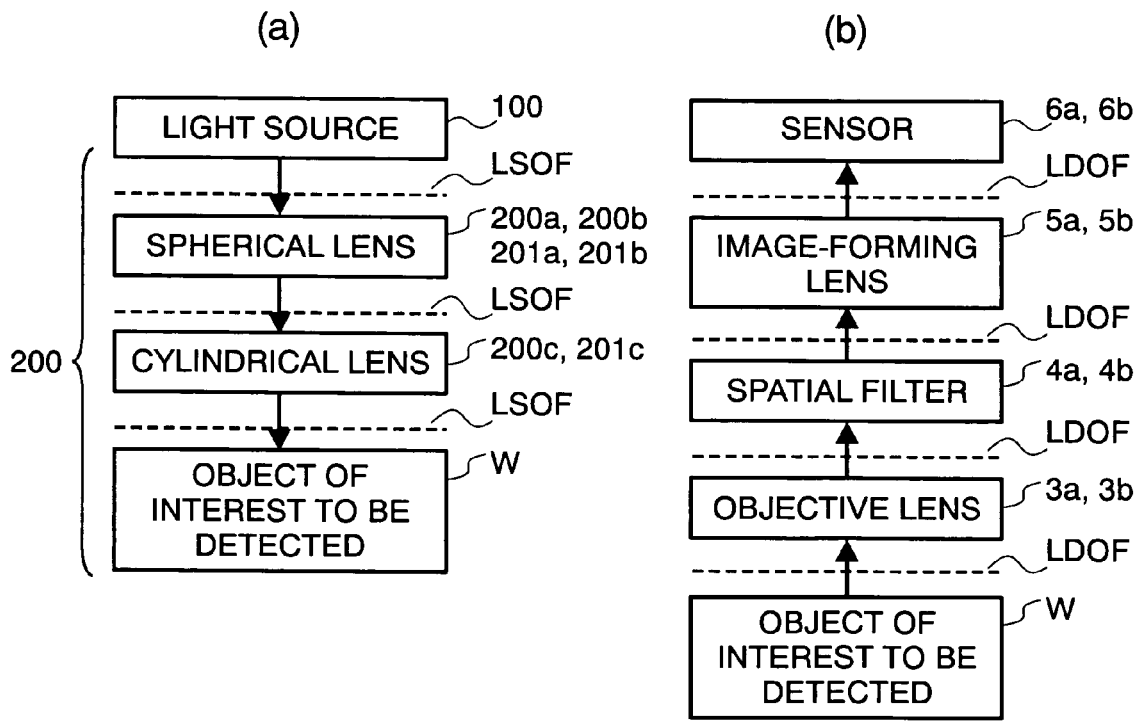
FIG. 27A is a block diagram showing a configuration of an illumination optical system.
FIG. 27B is a block diagram showing a configuration of a detection optical system.

The field of view SA2 of the oblique detection system 2001 (2) as shown in FIG. 25 is projected onto the substrate W of interest to be inspected at an elevation angle of detection β, and the corresponding detection area SA on the corresponding substrate W of interest for inspection is magnified by 1/sin β times. Thus, magnifying the detection area can expand an area per time scanned by the detector 6b (2), so that the substrate W of interest to be inspected can be detected at high speeds.

Figure 11:
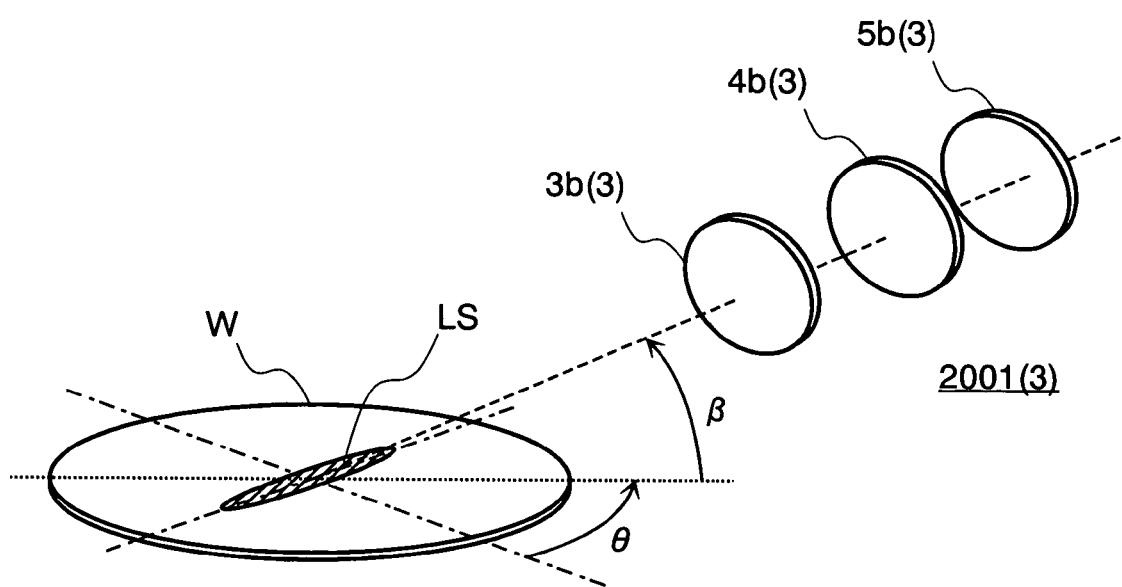
FIG. 11 is a perspective view for explaining a structure adapted for detection from the direction of an angle of θ with reference to the reference direction within the flat surface of the substrate of interest to be inspected.
Figure 12:
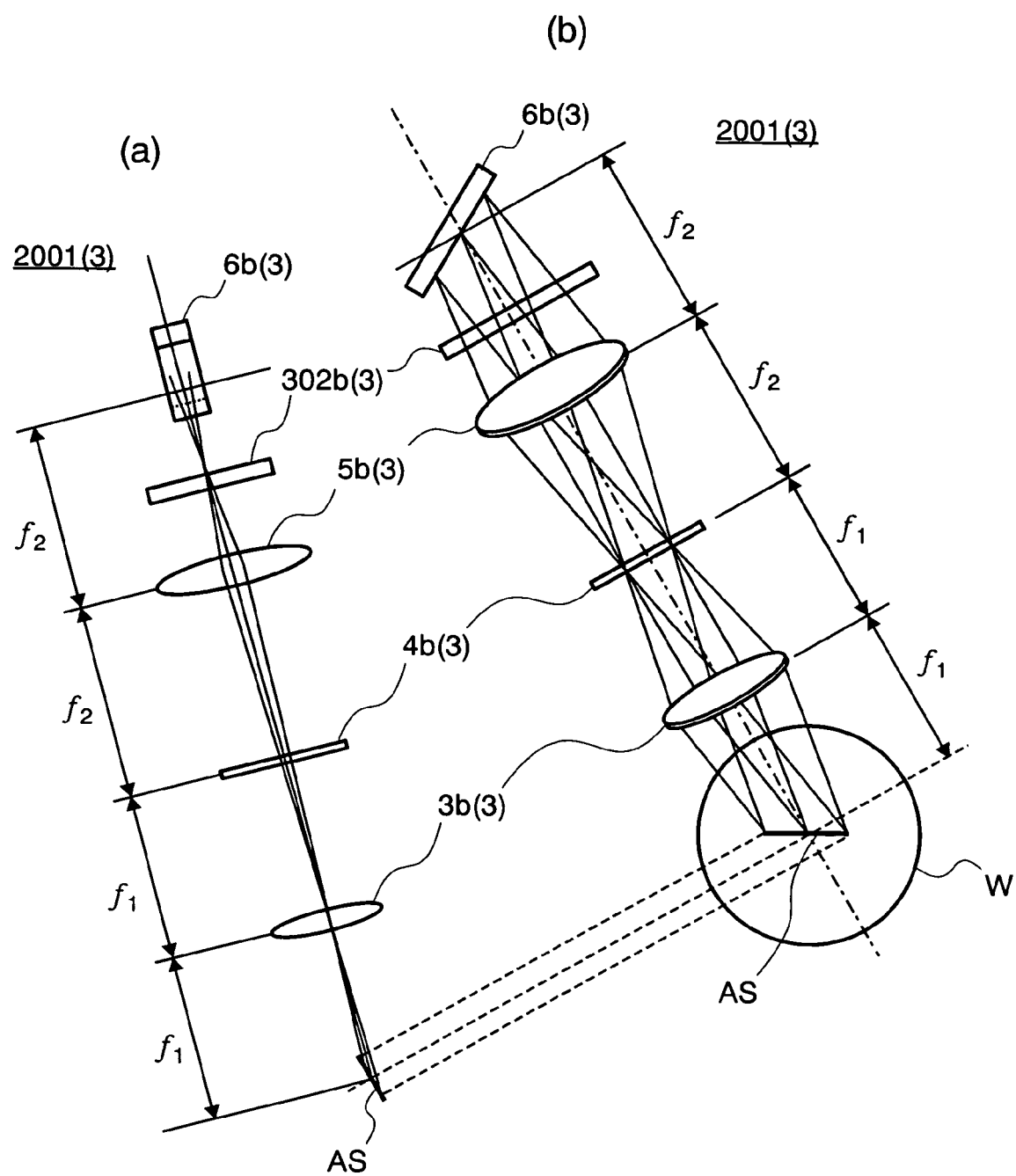
FIG. 12A is a schematic side view showing the structure of the detection optical system adapted for detection from the direction of an angle of θ with reference to the reference direction within the flat surface of the substrate of interest for inspection.
FIG. 12B is a schematic front view of the structure of the detection optical system.

Conversely, when the detection is intended to be carried out with high sensitivity and high accuracy by narrowing the detection area per time and enhancing the detection resolution, the detection area magnified by the detection elevation angle β needs to be narrowed. One of the methods for narrowing the detection area involves narrowing a field of view in the x direction by employing a field stop as the detection-light optical filter means 302b (2) installed on the optical path of the oblique detection system 2001. The second method, as shown in FIG. 26A, involves setting the width of the slit-like beam LS of the illuminating light in the x direction narrower than that of the detection area SA, and accumulating a signal at every distance corresponding to the width of illumination, thereby defining the width of the detection pixel by the illuminating light. This can narrow the width of the detection area expanded by the elevation angle narrower than the width of the SA defined by the oblique detection system 2001. FIG. 26B illustrates a relationship between the detection area SA and the shape of the slit-like beam LS when the detection resolution in the x direction is defined by the detection area SA. FIGS. 11 and 12 illustrate the oblique detection system 2001 (3) at times other than when the detection is carried out from the direction of azimuth angles of θ=0, 90, 180, and 270 degrees. FIG. 11 is a diagram for explaining the direction of detection. As shown in FIG. 12, the detector 6b is inclined in the longitudinal direction and in the direction perpendicular thereto in the two-dimensional manner, thereby enabling the detection from any direction.

Now, the relationship between the direction of the illuminating light by the oblique illumination system 1000, and the detection directions and the detection NAs of the upward detection system 2000 and the oblique detection system 2001 according to the embodiment of the invention will be explained in detail.

Figure 17:
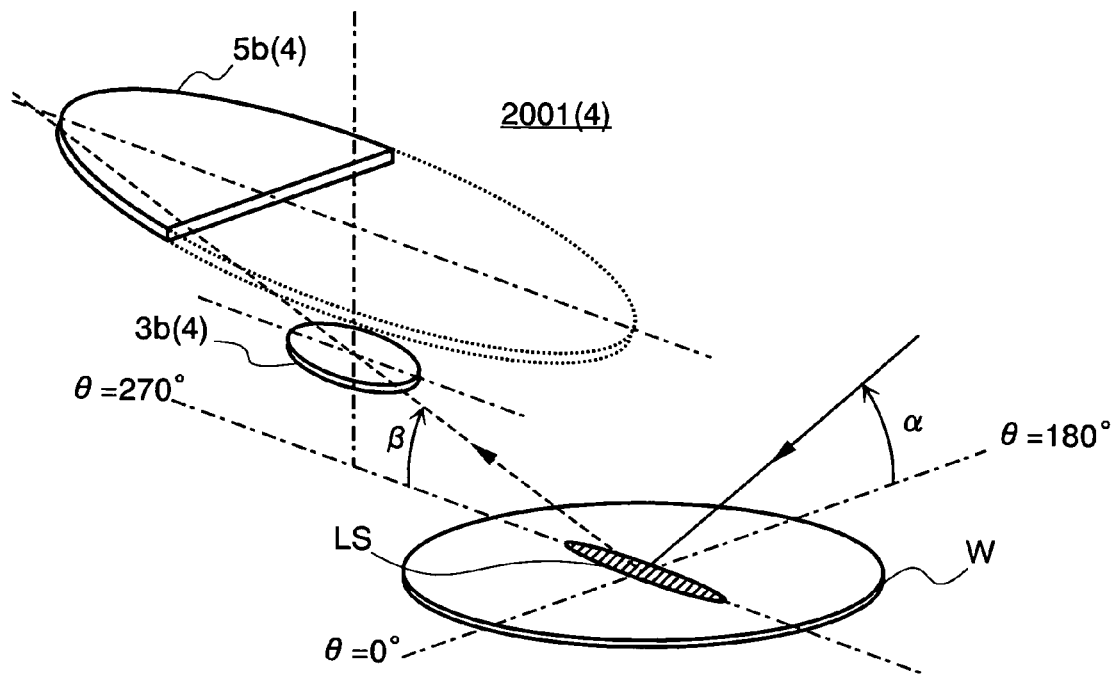
FIG. 17 is a perspective view showing a relationship between the substrate of interest to be inspected, and an image-forming lens and an objective lens of an oblique detection system adapted for detection in the direction of an angle of 270 degrees with respect to the reference direction within the flat surface of the substrate of interest to be inspected.
Figure 18:
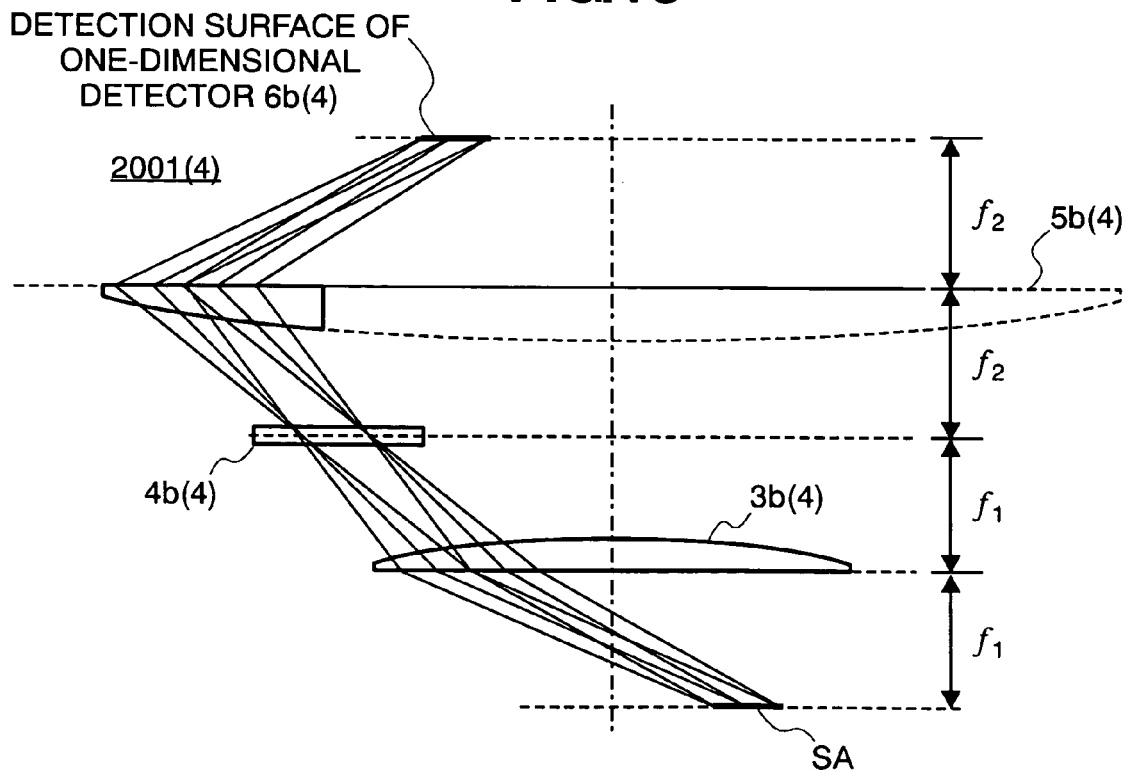
FIG. 18 is a schematic front view showing a structure of the oblique detection system adapted for detection in the direction of an angle of 270 degrees within the flat surface of the substrate of interest to be inspected.

FIGS. 17 and 18 illustrate another example of the configuration of an oblique detection system 2001 (4). The oblique detection system 2001 is configured to collect the light emitted from the illumination area LS on the substrate W of interest for inspection by the objective lens 3b, and to detect the light by the one-dimensional detector 6b, such as the TDI sensor, through the spatial filter 4b for blocking a Fourier transform image of the reflected and diffracted light from the repetitive pattern, and the image-forming lens 5b. In this example, the image-forming lens 5b is partially made from a large circular lens structure as shown in FIG. 9. As shown in FIG. 10, the objective lens 3b, the spatial filter 4b, and the image-forming lens 5b are arranged in parallel to the surface of the substrate W of interest to be inspected. The reflected and scattered light from the substrate W is detected above the substrate W of interest. At this time, the illumination area LS on the substrate W of interest for inspection shown in FIG. 3 provides an image on the detector 6b by the objective lens 3b constituting the relay lens, the spatial filter 4b, and the image-forming lens 5b. That is, the SA of FIG. 3 designates the light receiving area of the one-dimensional detector 6a, such as the TDI sensor.

FIG. 8A shows an illumination direction 700 with respect to the pattern P at an illumination azimuth angle of θ. A spherical surface 900 shown in FIG. 8B is virtual, and is to consider the positions of apertures of the objective lenses 3a and 3b in the upward detection system 2000 and the oblique detection system 2001. An intersection point of the spherical surface 900 and illuminating light 700 is a point 701. FIG. 8C shows the emission of the diffracted light of the illumination at an angle of θ=45 degrees. When the pattern P is a nonrepetitive pattern parallel to the y axis, the 0-order diffracted light is emitted in a direction of a ridge line of a cylinder having an illuminating point as a vertex, with an intersection point of the emission direction 901 of the regularly-reflected light and the virtual spherical surface 900 being set as a point 703, and the direction of the pattern (y direction) being positioned at the center. Thus, the intersection point with the virtual spherical surface 900 is positioned on a circle of the bottom of the cylinder. Therefore, this path is a line 704 parallel to the x axis as viewed from the direction of a normal line with respect to the substrate W of interest to be inspected. When the pattern P is the nonrepetitive pattern parallel to the y axis, the high-order diffracted light is emitted in a periodic direction of the pattern P at equal intervals, as designated by a dotted line 705 in FIG. 8C. The intensity of the diffracted light becomes large in the vicinity of the line 704 which represents the path of the 0-order light.

The aperture of the objective lens 3a in the upward detection system 2000 which is not inclined with respect to the direction of the normal line of the substrate W of interest to be inspected is an opening 800 shown in FIG. 8C. As shown in FIG. 8C, when the optical axis of the upward detection system 2000 is vertical to the surface of the substrate W of interest to be inspected, the relationship between the numerical aperture (NA) of the objective lens 3a and the elevation angle α of the illuminating light should be set based on a condition in which the 0-order diffracted light 703 in the x and y directions from the circuit pattern with its main group of lines oriented the x and y directions does not enter a pupil of the objective lens 3a, as shown in FIG. 8C. That is, the relationship between the numerical aperture (NA) of the objective lens 3a and the elevation angle α of the illumination light satisfies the following formula (1) with the angle θ of the illumination direction 700 being set to about 0 degree. This can prevent the 0-order diffracted light 704 in the x and y directions from the circuit pattern with its main group of lines oriented the x and y directions from entering the aperture 800 of the objective lens 3a even when the pattern is the nonrepetitive pattern.

$NA < \cos\alpha \cdot \sin\theta$, and $NA < \cos\alpha \cdot \sin(\pi/2 - \theta)$ (Formula 1)

Note that when the α is equal to or less than 30 degrees, the numerical aperture (NA) of the objective lens 3a may be equal to or less than about 0.6.

These conditions are valid especially in the defect detecting apparatus for a peripheral circuit area having a nonrepetitive pattern in a memory LSI, a CPU core area and input and output areas having nonrepetitive patterns in a LSI, such as a microcomputer, and a logic LSI having a nonrepetitive pattern. In most cases, such a LSI pattern is a pattern formed in parallel to the perpendicular direction (whose main group of lines are arranged perpendicularly), from which the 0-order diffracted light is emitted in a specific direction. Thus, by preventing the emitted 0-order diffracted light from entering the objective lens 3a, the diffracted light from these kinds of patterns is cancelled, thereby facilitating the detection of only the reflected and diffracted light from a defect, including foreign matter. More specifically, when the level of the detection signal from the circuit pattern is decreased, the defect including the foreign matter can be detected with high sensitivity. It should be noted that for the repetitive pattern, the high-order (the first-order, second-order, third-order, . . . ) diffracted light enters an aperture 800 of the objective lens 3a, and appears as a group of parallel lines 705 as shown in FIG. 8C. Then, such a high-order diffracted light may be blocked and cancelled by the band-like spatial filter 4a. The distances between the diffracted light spots and the positions thereof differ from one another depending on the size and shape of the pattern formed on the substrate W of interest to be inspected. The spatial filter 4a whose blocking pattern is changeable can be applied to various kinds of diffracted lights, the distances between the spots thereof and the positions thereof being different from one another, as disclosed in, for example, JP-A 218163/1993, and JP-A 258239/1994. Alternatively, some spatial filters 202 whose blocking patterns are different from each other may be previously prepared, and switched according to the circuit pattern. The use of the optical element that can be electrically controlled, such as a liquid crystal element, or a digital mirror device, can change the shape and size of the filter dynamically.

The aperture of the objective 3b in the oblique detection system 2001, which is inclined with respect to the direction of the normal line of the substrate W of interest to be inspected is an aperture 801 shown in FIG. 8C. In the embodiment, the detection azimuth angle is 270 degrees. The reason why the optical axis of the oblique detection system 2001 is inclined at an angle of β from the horizontal direction is that the high-order diffracted light is intended to be detected as compared with the case of the detection optical system 2000 which is not inclined with respect to the direction of the normal line of the substrate W of interest for inspection.

Now, azimuths of illumination and of detection will be described in detail. Generally, particles having a diameter of substantially not less than the wavelength of illumination tend to be forward scattered increasingly in the traveling direction of illumination. In contrast, particles having a diameter smaller than the wavelength of illumination (for example, a diameter of about one fourth of the wavelength) tend to be scattered isotropically in all directions. Therefore, when foreign matter or default having a size of not less than the wavelength is to be detected, the illumination and detection azimuths may be set so as to detect the forward scattering more than the other scattering. When the foreign matter or default that is sufficiently smaller than the wavelength is intended to be detected with high sensitivity, the illumination and detection azimuths should be set so as to block the scattered light from the pattern, which may interfere with the detection, and to detect the side or back scattering more than the other scattering, which is difficult to detect.

Figure 13:
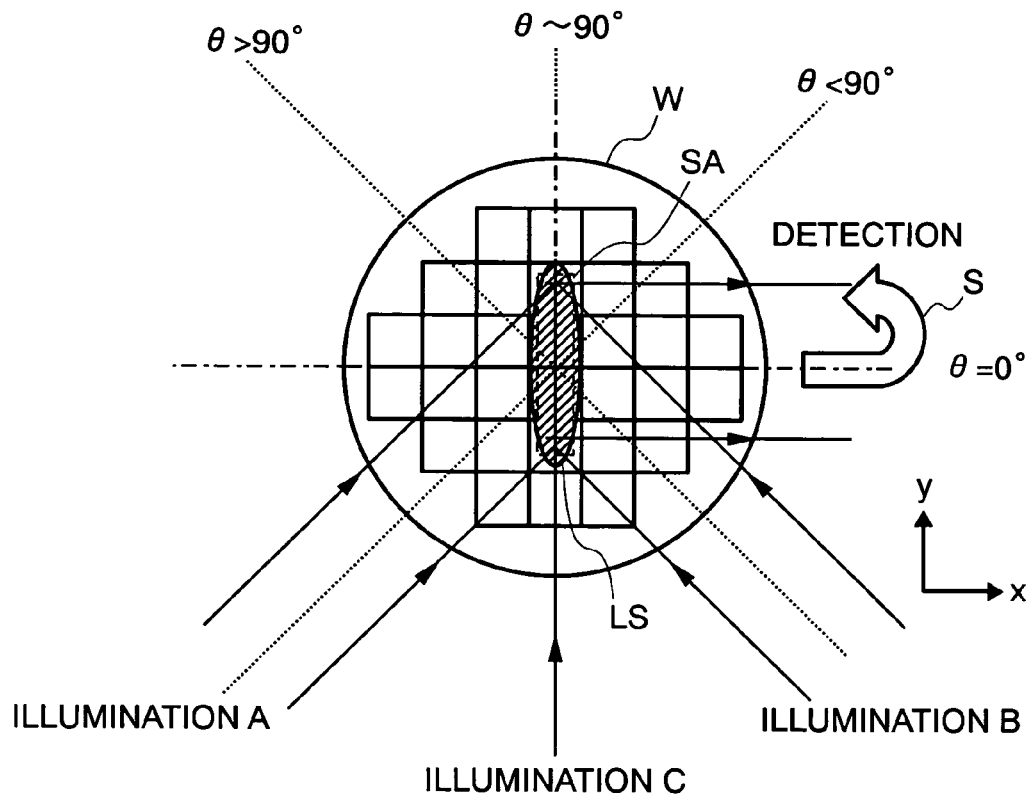
FIG. 13 is a plan view of the substrate of interest to be inspected, and showing a state in which a slit-like beam illuminates in a traveling direction of an angle of 45 degrees or 135 degrees with respect to the reference direction (θ=0 degree) within the flat surface of the substrate, and is detected from the direction of an angle of 0 degree.

As shown in FIG. 13, for the detection from the direction of zero degree (the detection at an azimuth angle of zero degree) the illuminating light (illumination A) enters the substrate in the direction of the azimuth angle of θ<90 degrees, so that the forward scattered light is detected. The illuminating light (illumination C) enters the substrate in the direction of the azimuth angle θ=about 90 degrees, so that the backward scattered light is detected. The illumination light (illumination B) enters the substrate in the direction of the azimuth angle of θ>90 degrees, so that the backward scattered light is detected. Thus, the switching among the illustration directions can change the sensitivity property to the size of the foreign matter or default. Furthermore, the illuminating light enters the substrate in the directions at the azimuth angle of θ<90 degrees and at the azimuth angle of θ<90 degrees at the same time, thereby enabling the detection of the default sufficiently smaller than the wavelength thereof as well as the default substantially equal to or above the wavelength thereof in a balanced manner. FIG. 13 illustrates a relationship among the illustration directions at the angle of θ=about 45 degrees (illumination A), θ=about 90 degrees (illumination C), and θ=about 135 degrees (illumination B), and the detection direction at the angle of θ=0 degree.

Figure 29:
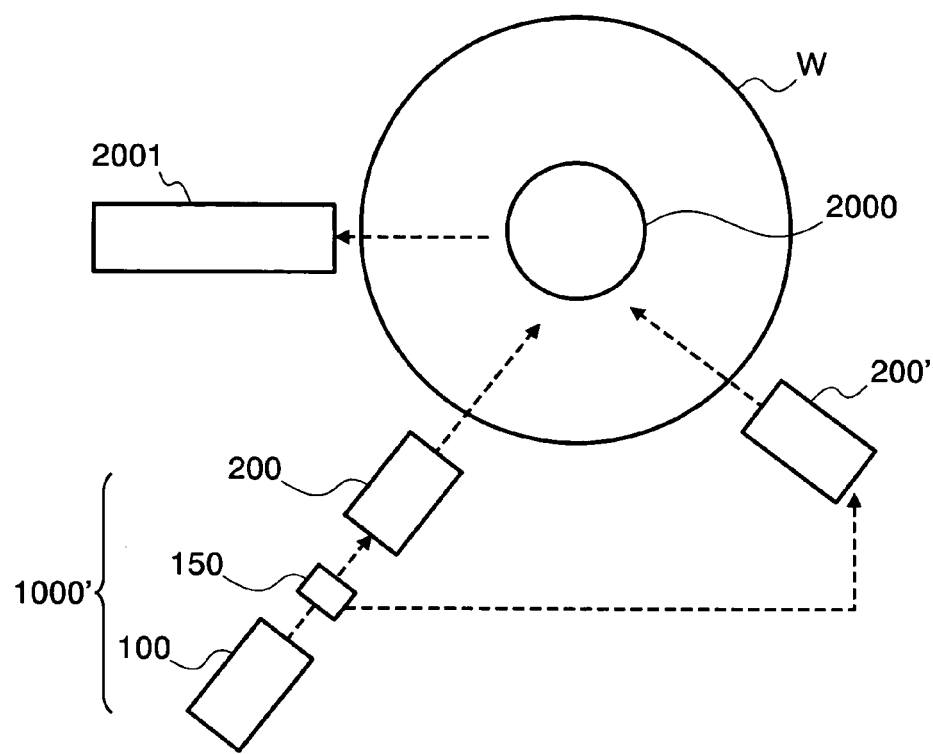
FIG. 29 is a substantial plan view of the defect detecting apparatus for explaining a positional relationship between the illumination system and the detection system when light illuminates from a plurality of azimuth angle directions.
Figure 30:
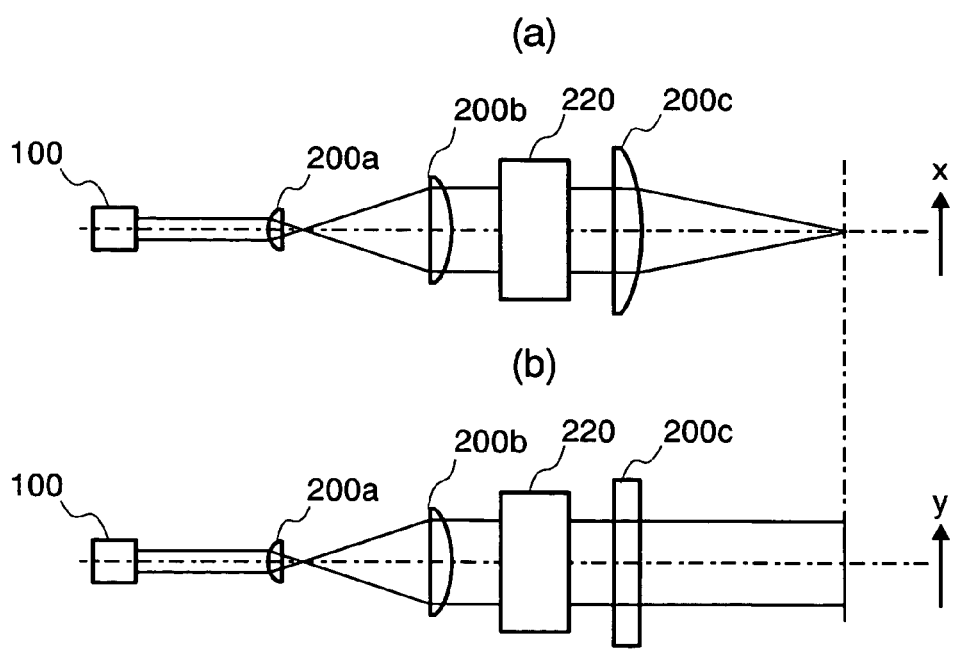
FIG. 30A is a schematic front view showing a configuration of a modification of the illumination optical system.
FIG. 30B is a schematic plan view showing a configuration of a modification of the illumination optical system.
Figure 32:
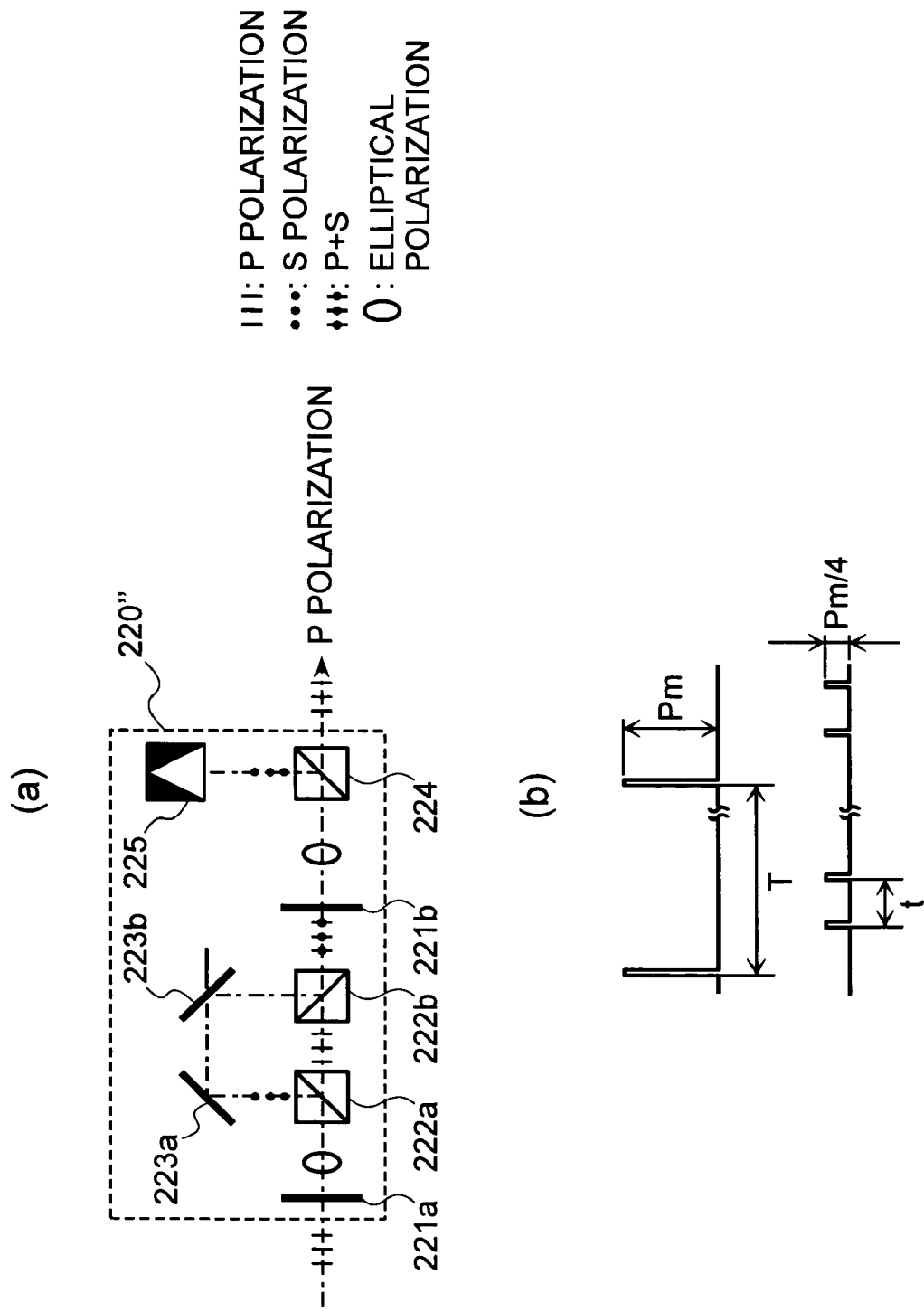
FIG. 32A is a schematic front view showing another modification of a pulse beam division optical system 200 which divides a pulse beam into two parts.
FIG. 32B illustrates a graph (on the upper stage) of the pulse shape of a pulse laser beam emitted from the light source 100, and a graph (on the lower stage) of the pulse shape of a P polarization pulse laser beam divided into two parts and emitted from a PBS 224.

FIG. 29 illustrates a positional relationship between the illumination optical system and the detection optical system when the illuminating light is applied from the two directions at different azimuth angles. An oblique illumination system 1000' has substantially the same function as that of the oblique illumination system 1000 shown in FIG. 1, but differs from the system 1000 in that an optical path branching element 150 is provided between the light source 100 and the lens system 200. With this arrangement, the illuminating light emitted from the light source 100 enters the optical path branching element 150 (for example, a beam splitter), which branches the light path into two paths. In one of the light paths, the light enters the lens system 200, and in the other, the light enters the lens system 200'. These lights are simultaneously applied to the same part on the substrate W of interest for inspection, that is, the area LS shown in FIG. 13 in a linear manner. The lens system 200' has the structure that conforms to that of the lens system 200.

The light reflected and scattered from the area LS in this illumination enters the upward detection system 2000 and the oblique detection system 2001, respectively, to be detected by these respective systems. Signals respectively detected by the upward detection system 2000 and the oblique detection system 2001 are processed in the same manner as that explained using FIG. 1. The use of the light source 100 is shared between the lens system 200 and the lens system 200', by which the lights applied to the substrate W of interest to be inspected have the same property to each other. Thus, the processing of the signals respectively detected by the upward detection system 2000 and the oblique detection system 2001 is relatively simple as compared with the case of independently using light sources.

On the other hand, alternatively, in the structure shown in FIG. 29, the total reflection mirror is employed in the optical path branching element 150 to switch the incident light to one of the two optical paths, thereby outputting the light therefrom. This can switch among the azimuth angles of illustration, thereby irradiating the substrate W of interest to be inspected with the light. Furthermore, in the structure of FIG. 29, the detection system may be either the upward detection system 2000 or the oblique detection system 2001.

Figure 16:
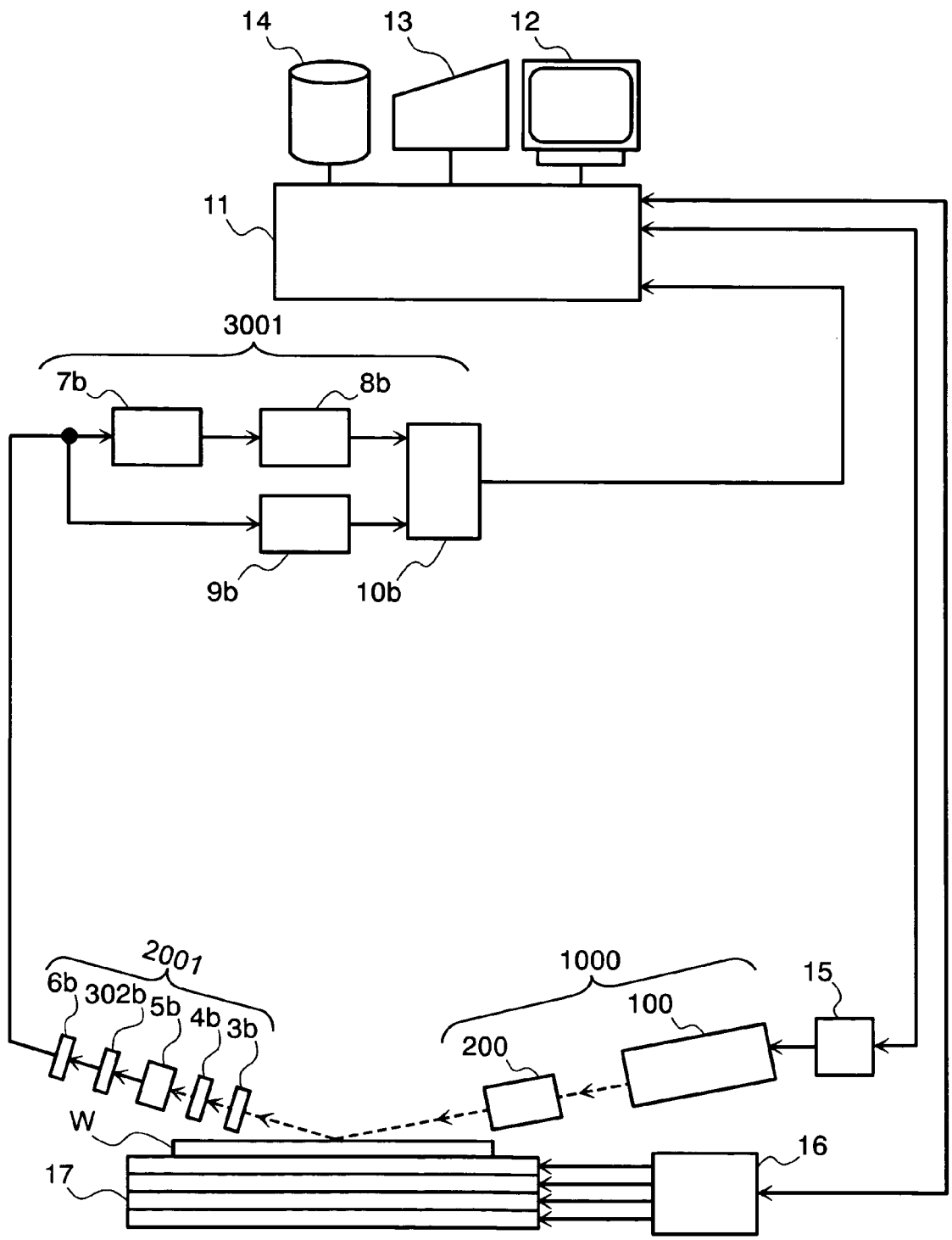
FIG. 16 is a schematic block diagram showing a structure of a first modification of the defect detecting apparatus according to the embodiment.

FIG. 16 illustrates a first modification of the detecting apparatus according to the embodiment of the invention. In this modification, the defect detecting apparatus includes the X-Y-Z-θ stage 17, the X-Y-Z-θ stage driver 16, an object to be detected (a semiconductor substrate of interest to be inspected) W, the light source driver 15, the oblique illumination system 1000, the oblique detection system 2001, the comparison processor for determination of defects 3000, the computer 11, the display 12, the central processing unit 13, and the storage device 14. This structure differs from the previous example in that the upper detection system 2000 explained in the structure shown in FIG. 1 is not provided. Since this structure does not include the upward detection system, it is less expensive than the structure of the previous example, and can detect the substrate of interest for inspection with the transparent film formed thereon with high sensitivity. In the structure shown in FIG. 16, elements designated by the same reference numerals as those of FIG. 1 have the same functions as those explained using FIG. 1. Also in this first modification, the illumination optical system can be applied which is composed of the oblique illumination system 1000' and the lens system 200' as explained in FIG. 29, and which irradiates the substrate W of interest for inspection from two directions at different azimuth angles.

Figure 28:
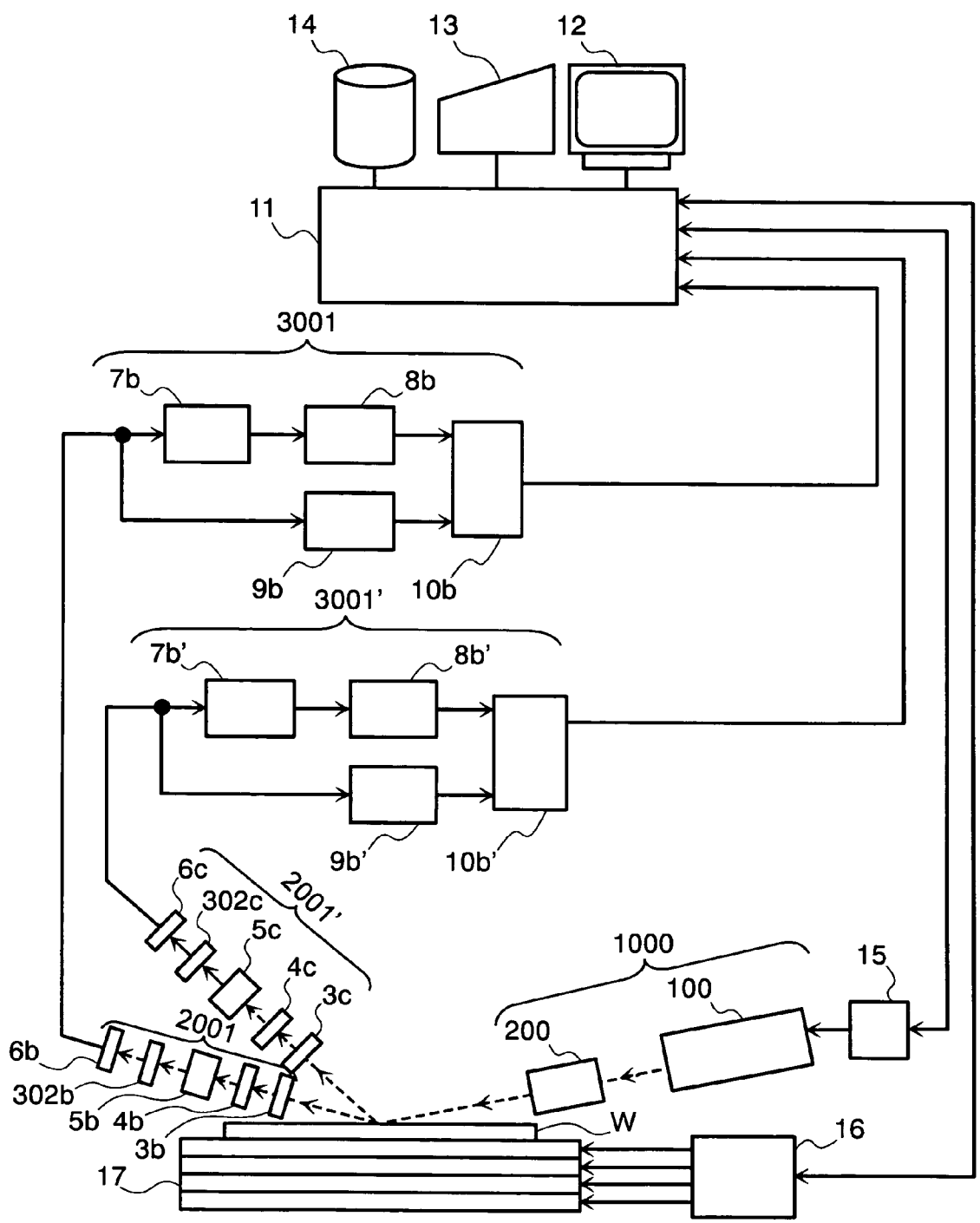
FIG. 28 is a block diagram showing a configuration of a second modification of the defect detecting apparatus according to the embodiment.

FIG. 28 illustrates a second modification of the detecting apparatus according to the embodiment of the invention. The defect detecting apparatus in this modification includes the X-Y-Z-θ stage 17, the X-Y-Z-θ stage driver 16, the object to be detected (the semiconductor substrate of interest to be inspected) W, the light source driver 15, the oblique illumination system 1000, the oblique detection systems 2001 and 2001', the comparison processors for determination of defects 3001 and 3001', the computer 11, the display 12, the central processing unit 13, and the storage device 14. The structure of this modification differs from the structure of the example shown in FIG. 1 in that two oblique detection systems 2001 and 2001' are provided without the detection optical system corresponding to the upward detection system 2000 explained in FIG. 1, and that the comparison processors for determination of defects 3001 and 3001' are provided corresponding to the respective oblique detection systems. A delay circuit 7b', a memory 8b', a memory 9b', and a comparison circuit 10b' constituting the comparison processor for determination of defects 3001' have the same respective functions as those of the delay circuit 7b, the memory 8b, the memory 9b, and the comparison circuit 10b, which constitute the comparison processor 3001 for determination of defects explained in FIG. 1. In this structure, the two oblique detection systems 2001 and 2001' are set to have different azimuth angles of detection, thereby simultaneously performing the detection of forward scattering and backward scattering. Furthermore, by comparing a defect signal provided by the detection of the forward scattering with a defect signal provided by the detection of the backward scattering, the size of the defect can be estimated. More specifically, this can be done using the principle of distribution of scattering angles that the larger the size of defect, the larger the ratio of the defect signal provided by the forward scattering detection.

With the arrangements described above, the intensity of light from the pattern detected by the oblique detection system 2001 can be relatively decreased as compared with the intensity of light from the pattern detected by the upward detection system 2000. Moreover, in these embodiments, the appropriate selection of the elevation angle a and polarization of the illuminating light, and the elevation angle β and polarization of detection can improve the sensitivity of detection of defects in a case where the transparent film is formed on the substrate W of interest to be inspected. This fact will be explained using FIGS. 19 to 22.

First, the selection of the elevation angle α and polarization of the illuminating light will be described below. FIG. 22A shows transmittance of S polarization and P polarization through a silicon oxide film ($SiO_2$) with respect to an incident angle when light enters the film from air. The larger the incident angle of each of the S polarization and P polarization, the smaller the transmittance into the film. The transmittance of the S polarization into the film is smaller than that of the P polarization.

Thus, decreasing the elevation angle α of the illuminating light can reduce the intensity of light proceeding into the film with respect to the intensity of light reflected from the film. Furthermore, the use of the S polarization can further decrease the intensity of light proceeding into the film. For example, for α=five degrees, the transmittances of the S polarization and the P polarization into the film are 28% and 50%, respectively. For α=three degrees, the transmittances of the S polarization and the P polarization into the film are 18% and 34%, respectively.

This can detect the defect signal indicative of the defect on the film with high sensitivity by relatively emphasizing the lighting of the defect on the film with respect to the pattern formed in the film, without being hidden in a scattered and diffracted light signal from the pattern in the film. The selection of the direction of polarization of the illumination is carried out by disposing and controlling a wavelength plate or a polarizing plate in the illumination optical system 200.

Although the illuminating at the low elevation angle as described above can decrease the intensity of the signal from the pattern in the film, when the pattern is still large as compared with the size of the defect to be detected, the diffracted and scattered light from the pattern in the transparent film may be detected in the form of a large signal intensity as compared to the defect.

As shown in FIG. 22B, also the light emitted from the inside of the transparent film at the low elevation angle has the smaller intensity of light. Therefore, the smaller the detection elevation angle β of the oblique detection system 2001, the smaller the intensity of the scattered light from the pattern in the transparent film can be set. Furthermore, selective detection of an S-polarization component, or setting the S polarization as a polarization state of illumination can further reduce the intensity of scattered light from the pattern in the transparent film. For example, when the polarization detected is S polarization and the detection elevation angle β is 15 degrees, the signal intensity from the pattern in the film can be decreased up to 60%, compared with the case of detection of the substrate W of interest for inspection from the direction of the normal line. Selection of the polarization to be detected can be carried out by installing an analyzer through which the light in a specific polarization condition is selectively transmitted, as the detection-light optical filter 302b.

As mentioned above, the illuminating at the low elevation angle and the detection at the low elevation angle can largely decrease the signal intensity from the pattern in the film, thereby selectively detecting only the defect on the transparent film.

When there are variations in thickness of the transparent film on the object W of interest to be inspected, the intensity of the diffracted and reflected light from the pattern to be detected may be varied due to the thin-film interference. For this reason, in determination of the defect, the comparison processing may be erroneously performed, which may result in misinformation on defects. This may be a cause of a decrease in sensitivity of detection. Accordingly, the elevation angle β of detection is set to an angle near a Brewster angle defined by the index of refraction of the transparent film, and the P-polarization component is selectively detected. This can reduce variations in brightness caused by the pattern in the transparent film due to a difference in thickness of the film. This method can detect the defects of the pattern in the film with high sensitivity. The principle of this method will be described below using FIGS. 19 to 21.

Figure 19:
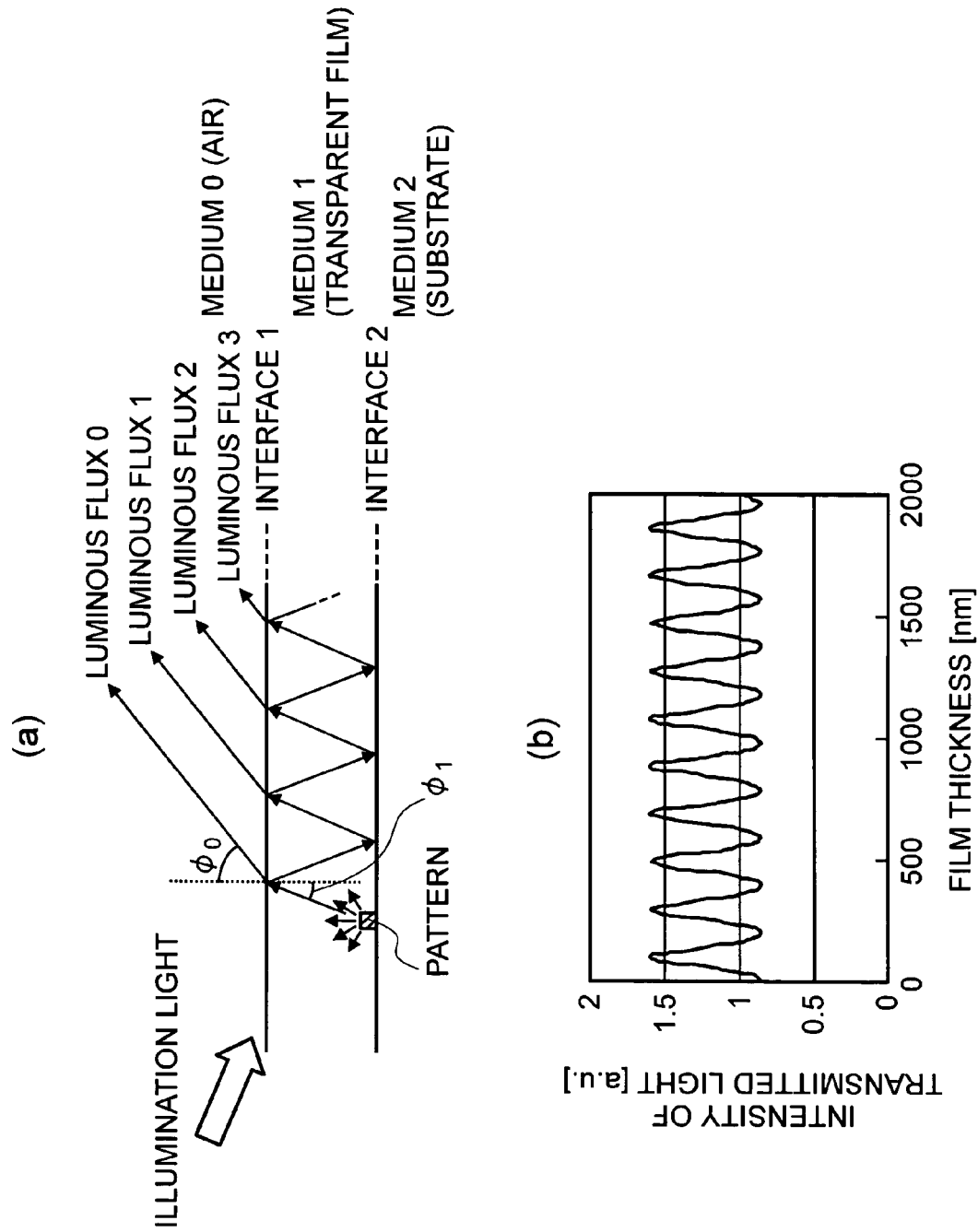
FIG. 19A is a sectional view of a specimen for explaining the occurrence principle of variations in brightness of a pattern in the transparent film.
FIG. 19B is a graph showing the dependency of variations in the intensity of transmitted light due to the thin-film interference on a film thickness.
Figure 20:
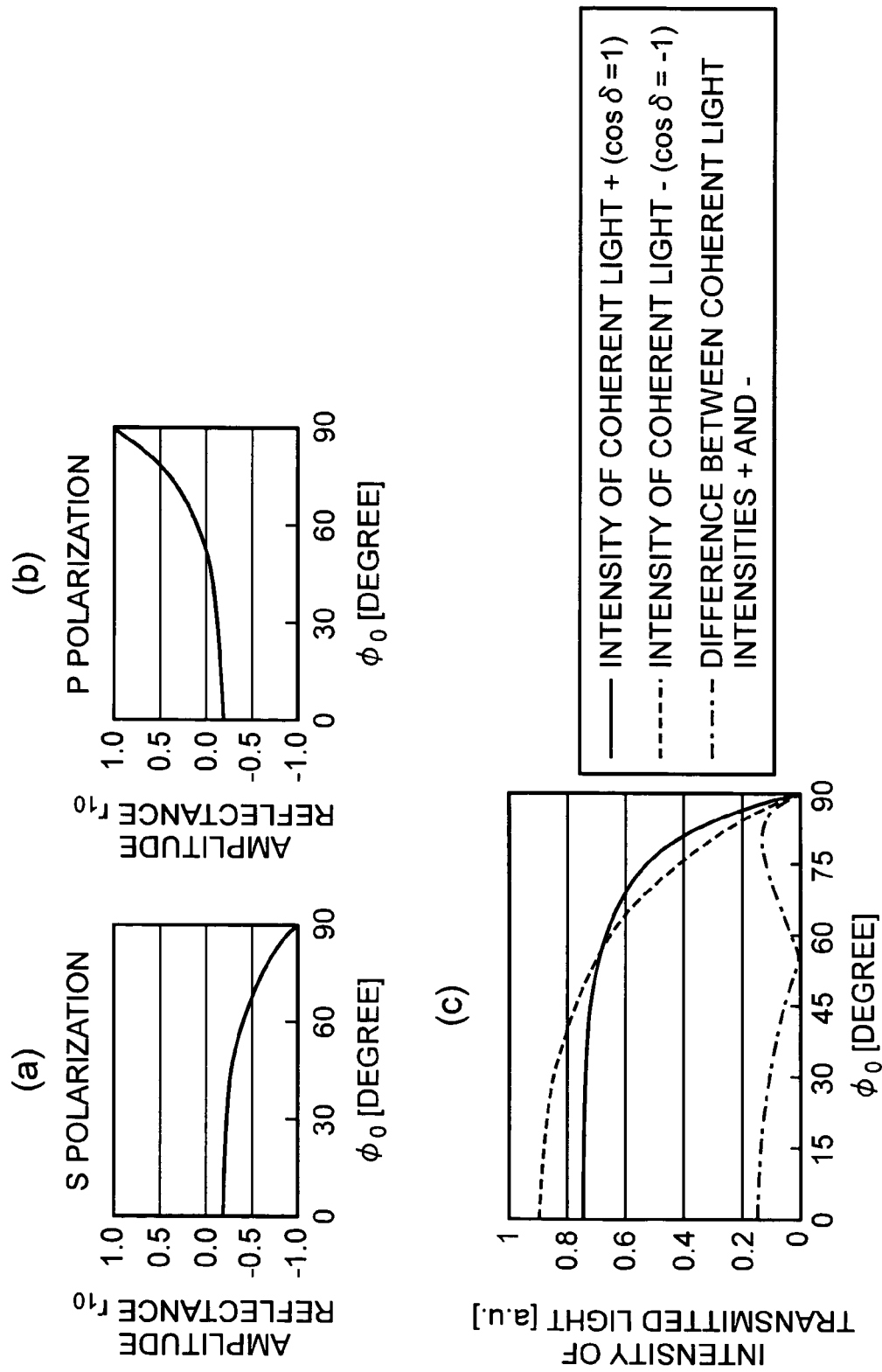
FIG. 20A is a graph showing a reflectance of S polarization at an interface of the transparent film, and the width of variations in the intensity of transmitted light when the S polarization illuminates.
FIG. 20B is a graph showing a reflectance of P polarization at an interface of the transparent film, and the width of variations in the intensity of transmitted light when the P polarization illuminates.
FIG. 20C is a graph representing a relationship between an emission angle $\phi_0$ of the light from the transparent film into the air and the intensity of light.
Figure 23:
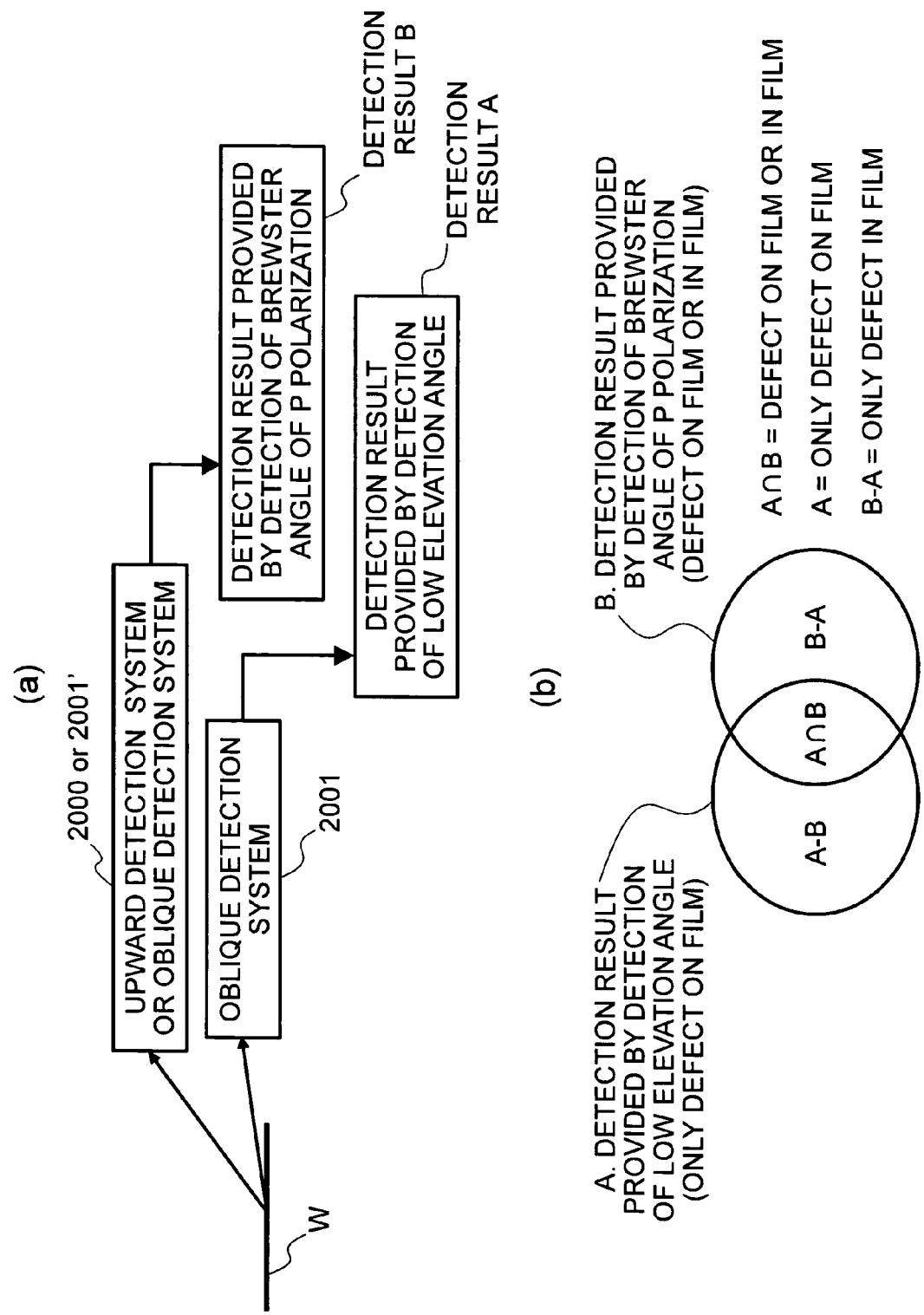
FIG. 23A is a block diagram showing a relationship of arrangement of the detection system with respect to the substrate of interest to be inspected, for individually detecting defects on and in the film.
FIG. 23B is a diagram explaining a method for classifying defects on and in the film.
Figure 24:
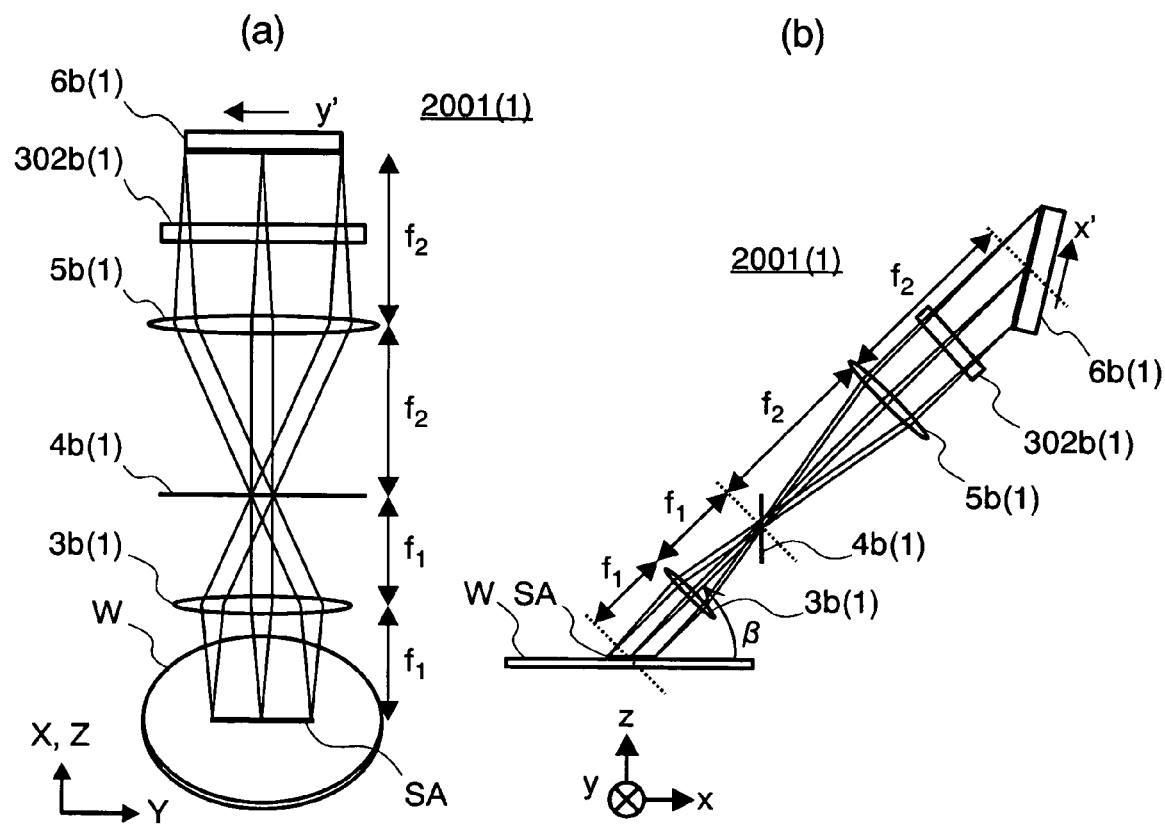
FIG. 24A is a perspective view of a detection optical system 2001(1) adapted for detection from the direction of an angle of zero degree with respect to the reference direction within the flat surface of the substrate of interest to be inspected.
FIG. 24B is a side view of the detection optical system 2001(1)

FIG. 19 is a diagram for explaining the thin-film interference by the transparent thin film. The pattern irradiated with the light from the oblique illumination system 1000 generates the diffracted and scattered light having a distribution of angles. FIG. 19A illustrates an optical path of a diffracted and scattered light component whose incident angle at an interface between the transparent film and the air is $\Phi_1$, and whose emission angle from the transparent film to the air is $\Phi_0$, that is, a light component observed in the direction of an angle of $\Phi_0$ with respect to the normal line of the substrate W of interest to be inspected. Interference arises between the transmitted light without being reflected at an interface between the air and the transparent film (interface 1), and the light reflected n times at the interface 1 and then transmitted through the interface 1. The change in the film thickness leads to a change in a difference of the optical path, which enhances or weakens the intensity of light depending on the film thickness. This is observed as variations in brightness.

In the structure shown in FIG. 19A, when an amplitude of the diffracted and scattered light generated from the pattern in the film is a0, an amplitude reflectance, and an amplitude transmittance of the light incident from a medium 1 to a medium 0 are r10, and t10, respectively, and an amplitude reflectance of the light incident from the medium 1 to a medium 2 is r12, a light component observed in the direction of an inclined angle of $\Phi_0$ with respect to the normal line of the substrate W of interest to be inspected, that is, the amplitude of an interference wave of luminous fluxes 0 to n is represented by the following formula (2). An intensity I of an interference light in the direction of an inclined angle of $\Phi_0$ with respect to the normal line of the substrate W of interest to be inspected is determined according to the following formula (3) using the formula (2).

$$at_{10} \sum_{n=0}^{\infty} [r_{10}r_{12}\exp(i\delta)]^n \qquad \text{(Formula 2)}$$

$$I = \frac{(at_{10})^2}{1+(r_{10}r_{12})^2 - 2r_{10}r_{12}\cos\delta} \frac{N_0\cos\varphi_0}{N_1\cos\varphi_1} \qquad \text{(Formula 3)}$$

where the above-mentioned amplitude reflectance and amplitude transmittance are determined by a Fresnel formula, depending on the refractive index of the medium and an incident angle thereof into an interface. The character δ used in the formulas 2 and 3 designates a difference in phase of transmitted adjacent lights, and is represented by the following formula (4) using a refractive index N1 of the medium 1, a film thickness d1, and a wavelength λ of the diffracted and scattered light. The formulas (3) and (4) show that a change in film thickness may cause a change in the intensity of the interference light. FIG. 19B shows an example of a change in brightness of the interference light with respect to variations in film thickness.

$$\delta = 4\pi N_1 d_1 \cos\phi_1/\lambda \qquad \text{(Formula 4)}$$

The formula (3) shows that the degree or size of variations in the brightness due to the film thickness depends on coefficients $r_{10}r_{12}$ for the term cos δ, and the smaller, the absolute value of the $r_{10}r_{12}$, the smaller the variations in the brightness becomes. Decreasing the absolute value of the $r_{10}r_{12}$ leads to decreasing the amplitude of the luminous flux n (n=1, 2, 3, . . . ) that interferes with the luminous flux 0 in FIG. 19A.

FIG. 20A is a graph showing dependency of the amplitude reflectance $r_{10}$ of the S polarization on the angle $\Phi_0$ at the interface 1 when the medium 0 is air, the medium 1 is the silicon oxide film ($SiO_2$), and the medium 2 is a silicon substrate (Si) FIG. 20B is a graph showing that of the P polarization. FIG. 20C shows a range of variations in the intensity of the light that is generated from the pattern in the film and emitted from the interface 1 in the direction of the angle of $\Phi_0$ when the medium 0 is air, the medium 1 is the silicon oxide film ($SiO_2$), and the medium 2 is a silicon substrate (Si). A solid line in FIG. 20C represents the intensity of the interference light when a difference in phase δ is zero degrees, whereas a dashed line represents the intensity of the interference light when a difference in phase δ is 180 degrees. The difference between these intensities indicates the variations in the intensity of the interference light, or the size of variations in the brightness, which is shown by a dashed-dotted line. When the angle $\Phi_0$ is about 56 ($\Phi_0$=56 degrees) (Brewster angle), the amplitude reflectance of the P polarization becomes zero. Thus, the P-polarization component of the diffracted and scattered light emitted in the direction of the Brewster angle does not cause variations in brightness due to the change in film thickness.

When the angle $\Phi_0$ is around the Brewster angle, the amplitude reflectance of the P polarization approaches zero. This significantly reduces the variations in the brightness of the P-polarization component of the diffracted and scattered light due to the change in the film thickness, which is emitted in the direction of the angle around the Brewster angle. For example, under the condition shown in FIG. 20B, when the size of variations in the brightness of the light is 1 at the angle $\Phi_0$ of 90 degrees, the sizes of the variations in the brightness of lights emitted at angles in ranges of 5 degrees, 10 degrees, and 15 degrees around the Brewster angle are 5%, 9%, and 14%, respectively.

Similarly, the angle $\Phi_0$ is set such that the angle $\Phi_1$ is the Brewster angle at the interface 2, and thus the reflectance r12 of the P polarization at the interface 2 approaches zero, thereby decreasing variations in the brightness.

The refractive index of the transparent film, such as a silicon oxide film ($SiO_2$), or a silicon nitride film ($Si_3N_4$), which is often used in a semiconductor process, does not change largely at a wavelength in a range including a DUV, a UV, and an optical wavelength (200 nm to 700 nm). Thus, the above-mentioned method for decreasing variations in the brightness can also be useful for multi-wavelength illumination including the DUV, the UV, and the optical wavelength, wideband illumination, or white illumination. Also in the second modification, the illumination optical system for irradiating the substrate W of interest to be inspected with light from two directions of different azimuth angles can be applied which comprises the oblique illumination system 1000' and the lens system 200' explained in FIG. 29. In this case, an appropriate combination of an azimuth angle of illumination and an elevation angle of detection is selected thereby to perform the detection. This can select the combination of the azimuth angle of illumination and the elevation angle of detection according to a defect to be detected, thereby improving the efficiency and accuracy of the detection.

When the illuminating light by the oblique illumination system 1000 is P polarization using the detection-light optical filter means 302b in the structure shown in FIG. 1, the ratio of the P-polarization component to the diffracted and scattered light from the substrate W of interest to be inspected becomes large. This can increase the amount of detection light for detection of only the P-polarization component, thereby detecting the defects of the pattern in the film with high sensitivity.

In order to decrease the variations in the brightness in detection, the above-mentioned structure may be used to selectively detect the P-polarization component of the diffracted and scattered light emitted in the direction of an angle from the normal line of the substrate W of interest corresponding to the angle $\Phi_0$, which is the Brewster angle. When the direction of the above-mentioned angle $\Phi_0$ is included within an angle range collectable by the objective lens 3a of the upward detection system 2000 with its NA, the selective detection can be carried out by the upward detection system 2000. When the direction of the above-mentioned angle $\Phi_0$ is not included within an angle range collectable by the objective lens 3a of the upward detection system 2000 with its NA, the selective detection can be carried out by the oblique detection system 2001.

The refractive index of the transparent film, such as a silicon oxide film ($SiO_2$), or a silicon nitride film ($Si_3N_4$), which is often used in a semiconductor process, is larger than one in a range of the DUV, UV, or optical wavelengths. Thus, the Brewster angle at the interface between the transparent film and the air is larger than 45 degrees, which is an emission angle on the air side. Therefore, in the structure shown in FIG. 1, in order to detect the diffracted and scattered light at this emission angle in the upward detection system 2000, it is necessary to use the objective lens 3a with a high NA of at least 0.7. The objective lens 3a with the high NA including the above-mentioned angle $\Phi_0$ is used, and a spatial filter means is further used as a spatial filter 4a for transmitting the diffracted and scattered light in a specific range of elevation angles over all azimuth angles, such as a spatial filter for selective detection of a high elevation angle (FIG. 21A), a spatial filter for selective detection of a middle elevation angle (FIG. 21B), and a spatial filter for selective detection of a low elevation angle (FIG. 21C) as shown in FIGS. 21A to C. This can transmit selectively only the light emitted in the direction of the angle $\Phi_0$, and detect only the P polarization using the analyzer, thereby decreasing the variations in the brightness, and detecting the defect. In this case, the substrate W of interest to be inspected with the transparent film formed thereon can be inspected with high sensitivity without using the oblique detection system 2000. Furthermore, this structure can detect the diffracted and scattered light components over all azimuth angles of an angle $\Phi_0$ from the normal line of the substrate W of interest for inspection, and thus has an advantage in a large amount of detection light.

When the direction of the above-mentioned angle $\Phi_0$ is not included within an angle range collectable by the objective lens 3a of the upward detection system 2000 with its NA, the detection elevation angle β of the oblique detection system 2001 is set to an angle corresponding to the angle $\Phi_0$, and only the P-polarization component is transmitted through the medium using the analyzer, the detection of defects can be done, while decreasing the variations in the brightness. In this case, the objective lens 3a with the high NA does not need to be used, and the upward detection system 2000 can be formed at a low cost. Additionally, since the NA of the upward detection system 2000 does not need to be limited, the oblique detection system 2001 can inspect a transparent-film forming area on the substrate W of interest for inspection with high sensitivity, and the upward detection system 2000 can detect an area where variations in brightness due to the transparent film are not problematic, with high sensitivity.

As shown in FIG. 23A, the detection of defects on and in the film is carried out by the detection of the Brewster angle of the P polarization using the upward detection system 2000 and the oblique detection system 2001' for selective detection of the high elevation angle as shown in FIG. 28. At the same time, the detection of defects on the film is carried out by the detection of the low elevation angle using the oblique detection system 2001. As shown in FIG. 23B, logical calculation of the detection results enables the simultaneous detection of defects on and in the film, the detection of only the defects on the film, which is categorized as the on-film defect among the on-film and in-film defects, and the detection of only the defects in the film.

Now, another modification of the illumination optical system 200 with the arrangement shown in FIGS. 1, 16, and 28 in use of a UV laser, such as a KrF laser, or an ArF laser, as the light source 100 will be described in detail with reference to FIGS. 30 to 33.

Since the amount of scattered light generating in the form of fine particles of 0.1 μm or less in diameter is inversely proportional to the fourth power of the illumination wavelength, the wavelength of illuminating light is shortened, thereby achieving the high sensitivity of detection. To enhance the detection sensitivity of defects, the UV laser whose wavelength is short may be used as a light source of illumination.

When a pulse oscillation laser is used as the UV laser, the pulse oscillation laser has the very high peak value (maximum output) with respect to the necessary average output. For example, when the laser has an average output of 2 [W], a pulse interval of 10 [ns], and a pulse width of 10 [ps] at an emission frequency of 100 MHz, the peak value (maximum output) of the laser is 2 [kW], which may damage the specimen. For this reason, the peak value (maximum output) is desired to be decreased, while keeping the average output.

In this modification, as shown in FIGS. 30A and B, a method for decreasing the peak value with the average output being kept involves magnifying the laser beam emitted from the light source 100 by the beam expander composed of the lens systems 200a and 200b, branching an optical path of the beam entering a pulse branching optical system 220 into a plurality of optical paths with different optical path lengths, thereby separating one pulse of the laser beam emitted from the light source into a plurality of pulses whose peak values are substantially the same, and irradiating the substrate W of interest to be inspected with a plurality of pulse lasers divided via the lens systems 200a, 200b, and 200c for forming the slit-like beam.

The pulse laser beam is divided into a plurality of beams to be applied. For example, the UV pulse laser beam with an emission frequency of 100 MHz is divided into a plurality of beams, and applied under the condition in which a traveling speed of the X-Y-Z-θ stage 17 on which the substrate W of interest to be inspected is put is 15 cm/sec, and a detection field of view per pixel of the detector 6a or 6b is 1 μm. Since the laser beams with 100 or more pulses are superimposed on each other and applied at an area to be detected by one pixel of the detector 6a or 6b, speckle noise caused by the laser beam is temporally averaged, and imaging can be carried out, thereby providing an image with the noise reduced.

A pulse-light division optical system 220 comprises a combination of ¼ wavelength plates 221a and 221b, PBSs (deflection beam splitters) 222a and 222b, and mirrors 223a and 223b, as shown in FIG. 31A. The laser beam magnified by the beam expander composed of the lens systems 200a and 200b, and entering in the form of a linear polarization (in this case, a P polarization) is formed into an elliptical polarization by the ¼ wavelength plate 221a, and then divided into the P polarization and the S polarization by the polarization beam splitter 222a. The P-polarization component, which is one of the divided polarizations, passes through the polarization beam splitter 222a and a polarization beam splitter 222b. The S-polarization component, which is the other of the divided polarizations, is reflected from the polarization beam splitter 222a, the mirror 223a, the mirror 223b, and the polarization beam splitter 22b, respectively, and returns to the same optical axis as that of the P-polarization component which passes through the polarization beam splitters 22a and 22b. At this time, when a distance between the polarization beam splitter 222a and the mirror 223a, and a distance between the polarization beam splitter 222b and the mirror 223b is set to L/2 [m], a difference in an optical path between the S-polarization component, and the P-polarization component is L [m]. When the light speed is represented by a reference character c [m/s], a difference in time between the S-polarization component and the P-polarization component is generated according to the formula (5).

$$t[s]=L[m]/c[m/s] \quad \text{(Formula 5)}$$

As shown in FIG. 31B, the pulse light can be time-shared, and its peak value can be reduced to one half.

For example, when a distance between the polarization beam splitter 222a and the mirror 223a, and a distance between the polarization beam splitter 222b and the mirror 223b are set to 15 cm (0.15 m), respectively, using a laser with a pulse interval of 10 ns (8 to 10 seconds), and with a pulse width of 10 ps (10 to 11 seconds), a difference in time between the S-polarization component and the P-polarization component is 1 ns (9 to 10 seconds). That is, a wafer surface is irradiated with a pulsing laser beam whose peak value is decreased to one half of its original value, at intervals of twice per nanosecond for 10 ns.

When the ratio of the S-polarization component to the P-polarization component of the incident beam into the polarization beam splitter 222a is set to 1:1 (circularly polarized light) by adjusting an angle of rotation of a ¼ wavelength plate 221a, the pulse light of the S-polarization component of a beam emitted from the polarization beam splitter 222b differs from the pulse light of the P-polarization component thereof in the peak value due to losses (of reflectance, and transmittance) of an optical component used (polarization beam splitters 222a and 222b, and the mirrors 223a and 223b). In order to decrease the maximum peak value of each pulse light, the peak values of the respective pulse lights needs to be substantially the same to each other.

In the structure of the pulse division optical system 200 shown in FIG. 31A, the P-polarization component is affected by the P polarization transmittance (Tp) of the polarization beam splitters 222a and 222b, and while the S-polarization component is affected by the S polarization transmittance (Rs) of the polarization beam splitters 222a and 222b, and the S polarization transmittance (Rm) of the mirrors 223a and 223b. A ratio of the loss of the S-polarization component to that of the P-polarization component (P1) is represented according to the following formula:

$$P1=Ls/Lp=Rm^2 \times Rs^2/Tp^2 \quad \text{(Formula 6)}$$

where Ls is a loss of the S-polarization component, and Lp is a loss of the P-polarization component. Thus, the peak value of the pulse light of the S-polarization component of the beam emitted from the polarization beam splitter 222b can be substantially equal to that of the P polarization component of the emitted beam by adjusting the rotation angle of the ¼ wavelength plate 221a such that the ellipticity of the incident beam polarization into the polarization beam splitter 222a is equal to the above-mentioned loss ratio. These pulse lights of the divided P and S-polarization components whose peak values are substantially identical to each other pass through the ¼ wavelength plate 221b to produce the circularly polarized light.

When linearly polarized light is used as the laser beam applied to the substrate W of interest to be inspected, a pulse division optical system 200' with the structure shown in FIG. 32A may be used. In this structure, the laser beam emitted from the light source 100 passes through an optical path which is defined by the polarization beam splitters 222a and 222b, and the mirrors 223a and 223b, which are the same as those shown in FIG. 31A, and is transmitted through the ¼ wavelength plate 221b to be changed into the circularly polarized light. The circularly polarized laser light enters the polarization beam splitter 224, thus causing only the P-polarization component thereof to pass through the splitter. The S-polarization component reflected from the polarization beam splitter 224, which may be stray light, is blocked by a beam trap 25. The P-polarization component divided by and passing through the polarization beam splitter 224 has its peak value decreased to one half of the peak value of the circularly polarized light entering the polarization beam splitter 224. Therefore, the peak value of the P-polarization component which has passed through the polarization beam splitter 224 is decreased to one fourth of the peak value of the pulse laser beam emitted from the light source 100 as shown in FIG. 32B.

In a case where only the S polarization is used, a ½ wavelength plate (not shown) is inserted after the polarization beam splitter 224 to rotate the direction of the polarization by an angle of 90 degrees. Alternatively, the polarization beam splitter 224 may be rotated around the center of an optical axis by an angle of 90 degrees (while, in this case, the position of insertion of the beam trap 25 is changed). If the polarization direction is optional, the emitted beam from the polarization beam splitter 222b may be used as it is. In this case, the peak value of the pulse laser light which is applied to the substrate W of interest to be inspected is one half of the peak value of the pulse laser beam emitted from the light source 100 .

Although the pulse light is divided into two lights using the pulse division optical systems 200 or 200' in the above description, the invention is not limited thereto. In order to increase the number of divisions of the light, a method for dividing the light into four lights using a modification of the pulse division optical system 200 will be described below with reference to FIGS. 32A and 32B. The structure of a pulse division optical system 200" shown in FIG. 33A is composed of two stages, each stage comprising the pulse division optical system 200 shown in FIG. 31A. A distance between the polarization beam splitter 222c and the mirror 223c of the second stage, and a distance between the polarization beam splitter 222d and the mirror 223d thereof are twice as long as that between the polarization beam splitter 222c and the mirror 223c of the first stage, and that between the polarization beam splitter 222d and the mirror 223d thereof, respectively. The beam emitted from the polarization beam splitter 222b of the first stage is an S polarized pulse light that is delayed in time from a P polarized pulse light. The pulse light string is formed into the circularly polarized light by the ¼ wavelength plate 221b. Thus, a part of the pulse light string transmitted through the ¼ wavelength plate 221b to have its intensity which is one half of that of the pulse light string is the P polarization. The P polarization is transmitted through the polarization beam splitters 222c and 222d. On the other hand, a remaining part of the pulse light string transmitted through the ¼ wavelength plate to have its intensity which is one half of the pulse light string is the S polarization. The S polarization is reflected from the polarization beam splitters 222c and 222d and the mirrors 223c and 23d to return to the same optical axis. Thus, as shown in FIG. 33B, the pulse light is divided into four lights, each of which has its peak value that is decreased to one fourth of that of the pulse laser beam emitted from the light source 100. Strictly speaking, as mentioned above, due to the loss by the optical component, the peak value is decreased to less than one fourth of that of the pulse laser beam.

In the structure shown in FIG. 33A, P polarized pulse laser light passing through the polarization beam splitter 222d after the polarization beam splitter 222c, and S polarized pulse laser light reflected by the mirror 223d and by the polarization beam splitter 222d enter the ¼ wavelength plate 221c through the same optical axis, so that respective circularly polarized lights are emitted from the pulse division optical system 200″. On the other hand, the circularly polarized light emitted from the ¼ wavelength plate 221c enters a polarization beam splitter (not shown), which corresponds to the polarization beam splitter 224 shown in FIG. 32A, to be separated into the P-polarization component and the S-polarization component. This can irradiate a wafer 1 with only the P-polarization component. (In this case, the peak value of a pulse beam of the P-polarization component divided by the above-mentioned polarization beam splitter not shown is one eighth of that of the pulse laser beam emitted from the light source 100.)

Restrictions imposed on the above-mentioned examples are the following two points. First, an optical path difference (L) in the first stage is longer than a coherence length of laser light used (Λ) as shown in the following formula (7)

$$L > \Lambda = \lambda^2/\Delta\lambda \quad \text{(Formula 7)}$$

where λ is a wavelength, and Δλ is a range of wavelengths. Secondly, the pulse light string divided is within an oscillation interval of the laser as shown in the following formula (8).

$$L(n+1) < c \cdot (1/f) \quad \text{(Formula 8)}$$

where L is an optical path difference in the first stage, n is the number of stages, c is the light speed, and f is an oscillation frequency of the laser.

According to the embodiments of the invention, since the UV pulse laser beam can be applied to the wafer with its peak value decreased, micro-defects of less than 0.1 μm in diameter can be detected without damaging the wafer.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

The invention claimed is:

1. A method for detecting a defect, comprising the steps of:
irradiating a slit shaped area on a specimen with a circuit pattern including a repetitive pattern formed thereon which is covered with an optically transparent film with a slit shaped light from an oblique direction;
detecting light scattered from the specimen by the irradiation of light in a direction of a first elevation angle with respect to said specimen by blocking light diffracted from said repetitive pattern, among light from the specimen, thereby obtaining a first detection signal;
detecting light scattered from the specimen by the irradiation of light in a direction of a second elevation angle which is lower than said direction of the first elevation angle with respect to said specimen by blocking light diffracted from said repetitive pattern, among light from the specimen, thereby obtaining a second detection signal; and
processing said first detection signal and said second detection signal to detect a defect including foreign matter on the specimen,
wherein in the step of detecting light scattered from the specimen in a direction of the second elevation angle, said second elevation angle is set so as to reduce detection of light scattered from inside the optically transparent film.

2. The method for detecting a defect according to claim 1, wherein in the step of detecting light scattered from the specimen in a direction of the first elevation angle, said light diffracted from said repetitive pattern is blocked by a spatial filter.

3. The method for detecting a defect according to claim 1, further comprising a step of detecting the defect including foreign matter that is smaller than a wavelength of the irradiated light by detecting backscattered light from the specimen irradiated with the light formed toward the one direction in the long shape.

4. An apparatus for detecting a defect, comprising:
a light source adapted to emit illuminating light;
table means for putting a specimen with a circuit pattern including a repetitive pattern formed thereon which is covered with an optically transparent film;
irradiating means for forming the illuminating light emitted from the light source to a slit like shape, and for irradiating a slit like area on the specimen put on the table means with the slit like shaped light from an oblique direction;
first detection means for detecting light scattered from the slit like area on the specimen irradiated with the slit like shaped light in a direction of a first elevation angle with respect to the specimen by blocking light diffracted from the repetitive pattern, among light from the specimen irradiated by the irradiating means;
second detection means for detecting light scattered from the slit like area on the specimen irradiated with the slit like shaped light in a direction of a second elevation angle which is lower than said direction of the first elevation angle with respect to the specimen by blocking light diffracted from said repetitive pattern, among light from the specimen irradiated by the irradiating means; and
signal processing means for processing a first detection signal obtained by the detection of the light from the slit like area on the specimen by said first detection means, and a second detection signal obtained by the detection of the light from the slit like area on the specimen by said second detection means, thereby detecting a defect including foreign matter on the specimen,
wherein said second elevation angle is set so as to reduce detection of light scattered from inside the optically transparent film.

5. The apparatus for detecting a defect according to claim 4, wherein said light source emits pulse laser light, and
wherein said irradiating means includes a pulse division unit for dividing one pulse of the pulse laser light emitted from the light source into a plurality of pulses, and is adapted to irradiate the specimen with the laser light whose pulse is divided into the plurality of pulses by said pulse division unit.

6. The apparatus for detecting a defect according to claim 5, wherein said pulse division unit is adapted to divide one pulse of the laser light emitted from the light source into the plurality of pulses by introducing the pulse laser light emitted from the light source into a plurality of optical paths with different optical path lengths.

7. The apparatus for detecting a defect according to claim 4, wherein said first detection means includes a spatial filter for blocking light diffracted from the repetitive pattern formed on the specimen irradiated with the slit like shaped light.

8. The apparatus for detecting a defect according to claim 4, wherein said detection means is a TDI sensor subjected to an anti-blooming process.

* * * * *